United States Patent
Inaba et al.

(10) Patent No.: US 6,808,610 B2
(45) Date of Patent: Oct. 26, 2004

(54) CAPILLARY ARRAY ELECTROPHORESIS APPARATUS

(75) Inventors: Ryoji Inaba, Hitachinaka (JP); Satoshi Takahashi, Hitachinaka (JP); Miho Ozawa, Abiko (JP); Yoshitaka Kodama, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 548 days.

(21) Appl. No.: 09/815,329

(22) Filed: Mar. 23, 2001

(65) Prior Publication Data

US 2001/0040094 A1 Nov. 15, 2001

(30) Foreign Application Priority Data

May 15, 2000 (JP) ..................................... 2000-147494

(51) Int. Cl.[7] .......................................... G01N 27/447
(52) U.S. Cl. ...................... 204/603; 204/601; 356/344
(58) Field of Search ............................. 204/600, 601, 204/603, 452; 356/344

(56) References Cited

U.S. PATENT DOCUMENTS

| | | | |
|---|---|---|---|
| 5,312,535 A | | 5/1994 | Waska et al. |
| 5,366,603 A | * | 11/1994 | Middendorf et al. ........ 204/461 |
| 5,567,294 A | * | 10/1996 | Dovichi et al. ............ 204/603 |
| 5,582,705 A | | 12/1996 | Yeung et al. |
| 5,600,444 A | * | 2/1997 | Tong .......................... 356/432 |
| 5,621,831 A | * | 4/1997 | Staver et al. .................. 385/33 |
| 5,790,727 A | * | 8/1998 | Dhadwal et al. .............. 385/38 |
| 5,833,827 A | | 11/1998 | Anazawa et al. |
| 5,938,908 A | | 8/1999 | Anazawa et al. |
| 6,358,387 B1 | * | 3/2002 | Kopf-Sill et al. ........... 204/603 |
| 6,592,733 B1 | * | 7/2003 | Foley et al. ................ 204/603 |

FOREIGN PATENT DOCUMENTS

| | | | | |
|---|---|---|---|---|
| FR | 2774472 A1 | * | 8/1999 | ............. C02F/1/40 |
| JP | 9-96623 | | 4/1997 | |
| JP | 9-152418 | | 6/1997 | |
| JP | 9-288088 | | 11/1997 | |
| JP | 10-160705 | | 6/1998 | |
| JP | 2000-97908 | | 4/2000 | |

OTHER PUBLICATIONS

Ueno et al. "Simultaneous Monitoring of DNA Fragments Separated by Electrophoresis in a Multiplexed Array of 100 Capillaries," Anal. Chem. 1994, 66, 1424–1431.*

* cited by examiner

*Primary Examiner*—Nam Nguyen
*Assistant Examiner*—Brian L. Mutschler
(74) *Attorney, Agent, or Firm*—Dickstein Shapiro Morin & Oshinsky LLP

(57) ABSTRACT

When irradiating laser beam from the side face of the capillary array, an optical axis of the laser beam is inclined in vertical direction with respect to a plane face formed by the capillary array, thus, reflection light by the capillary array and returning light is prevented from entering into a laser beam source, thereby, instability of laser oscillation is eliminated.

44 Claims, 18 Drawing Sheets

FIG. 4A
FIG. 4B
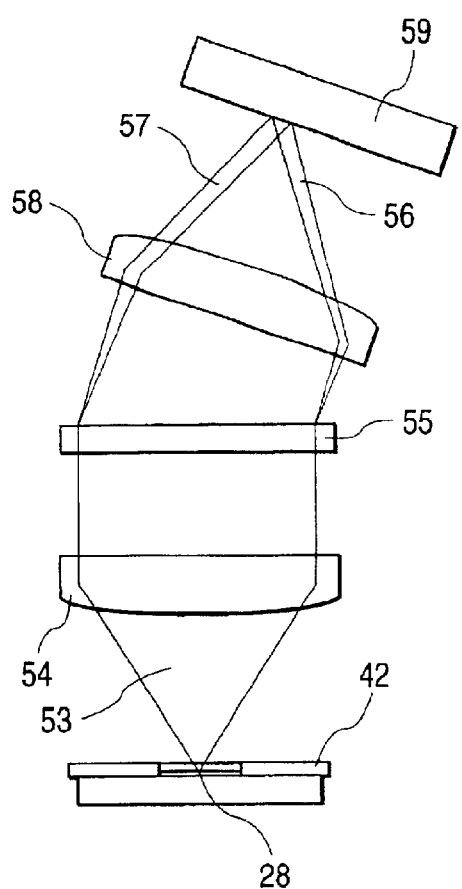
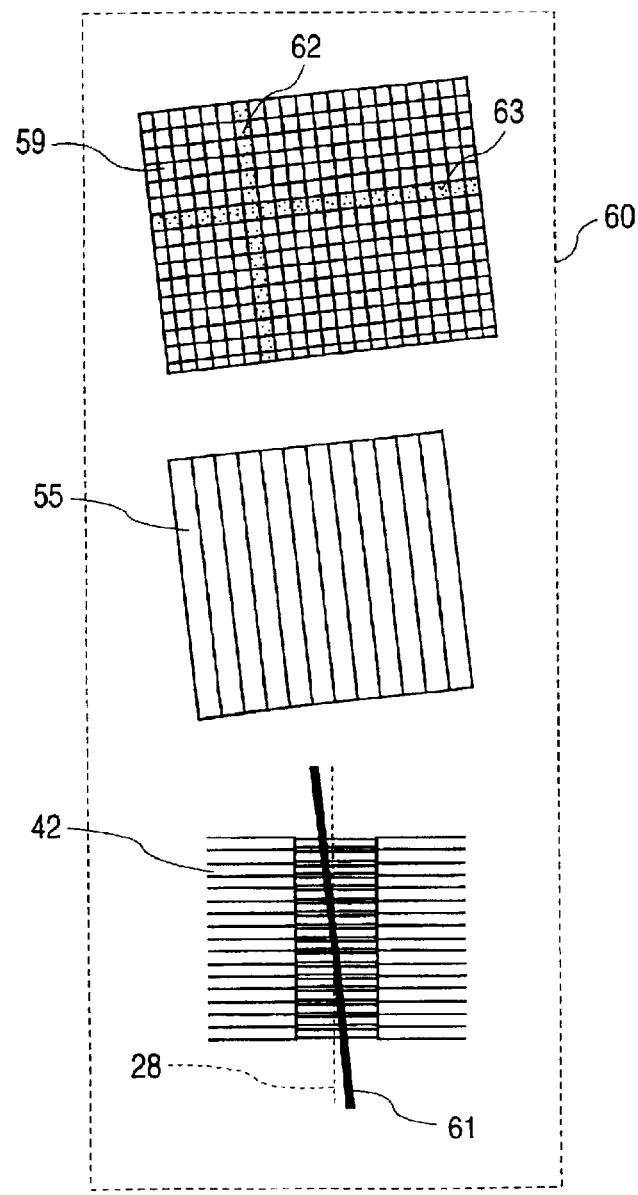

(DETECTOR IS BACK OF SHEET)

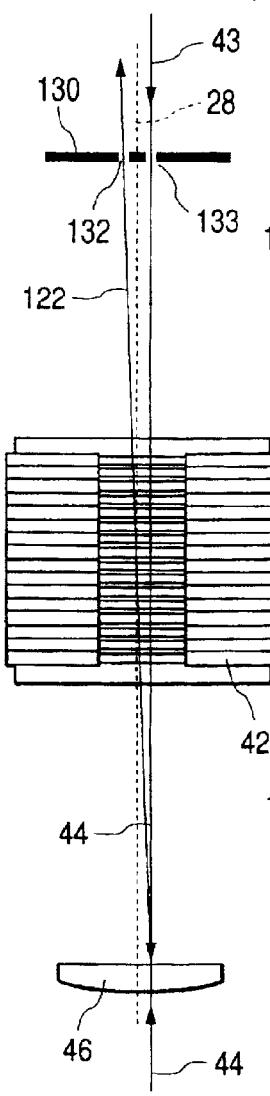
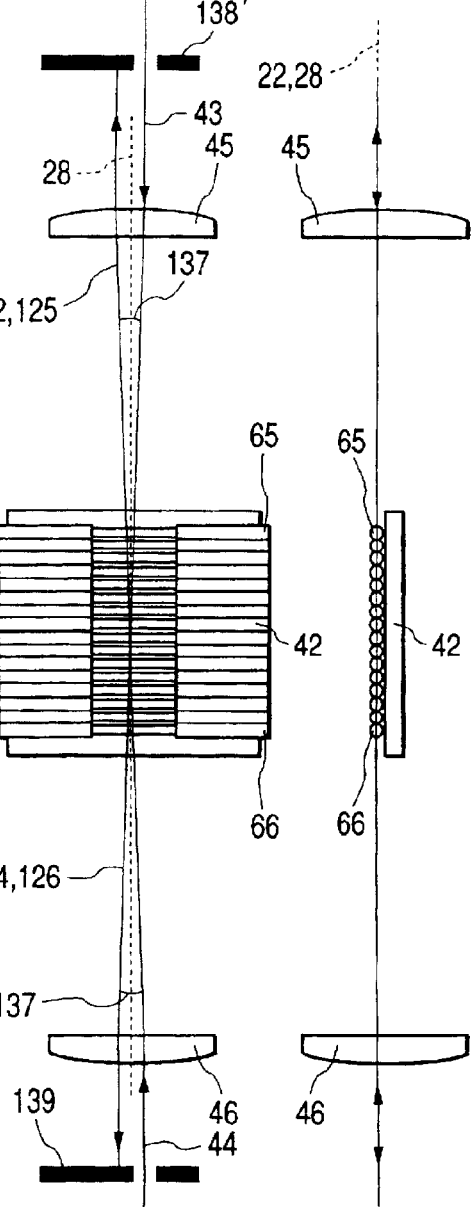
FIG. 10A FIG. 10B FIG. 10C FIG. 10D

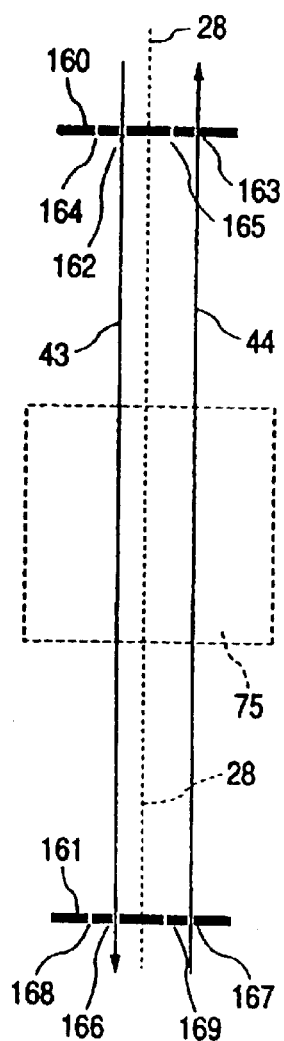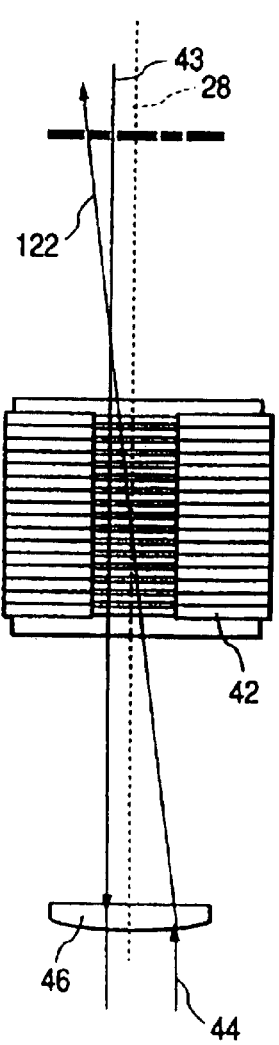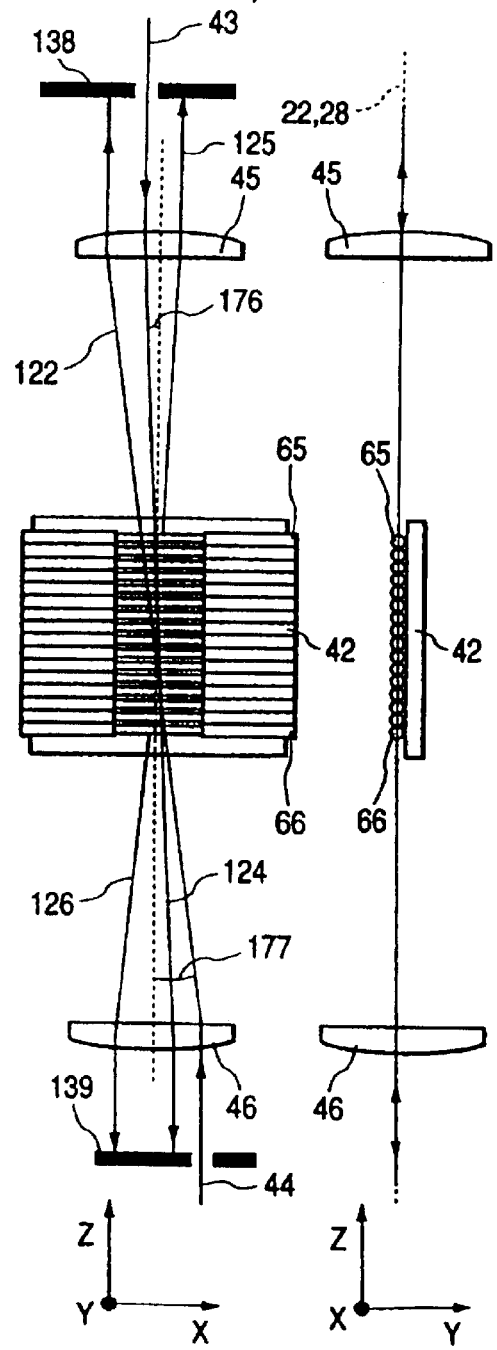
FIG. 13A FIG. 13B FIG. 13C FIG. 13D

FIG. 15A
FIG. 15B
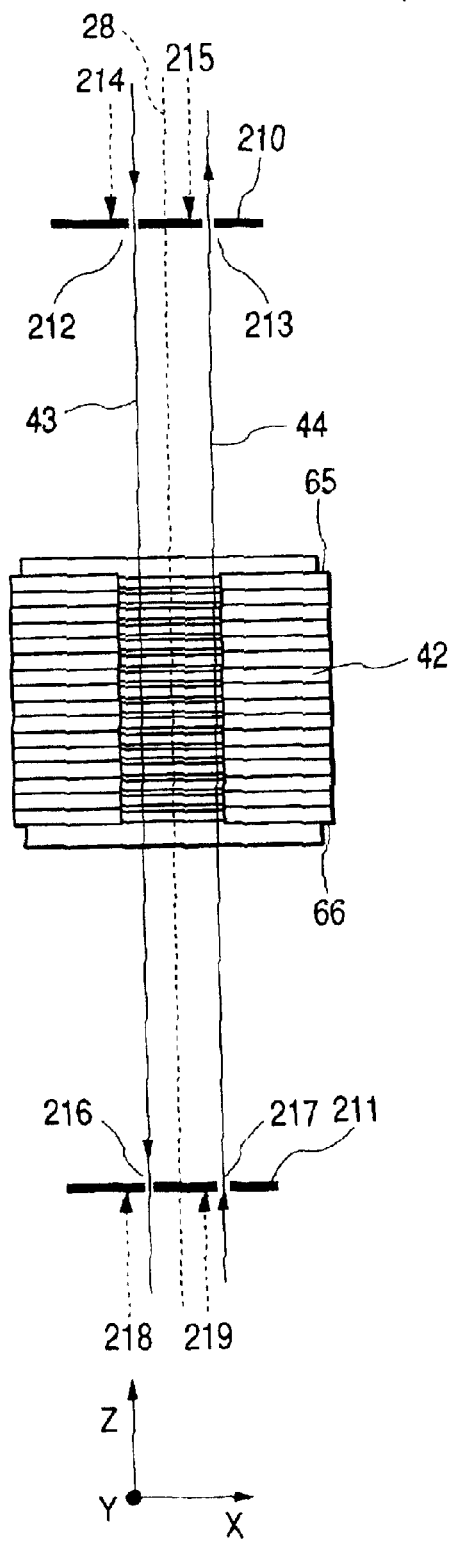
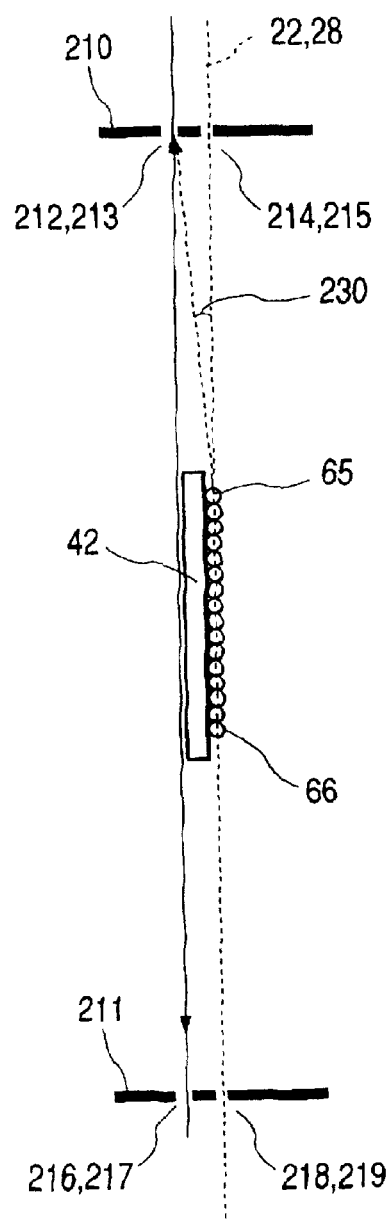

FIG. 15C
FIG. 15D
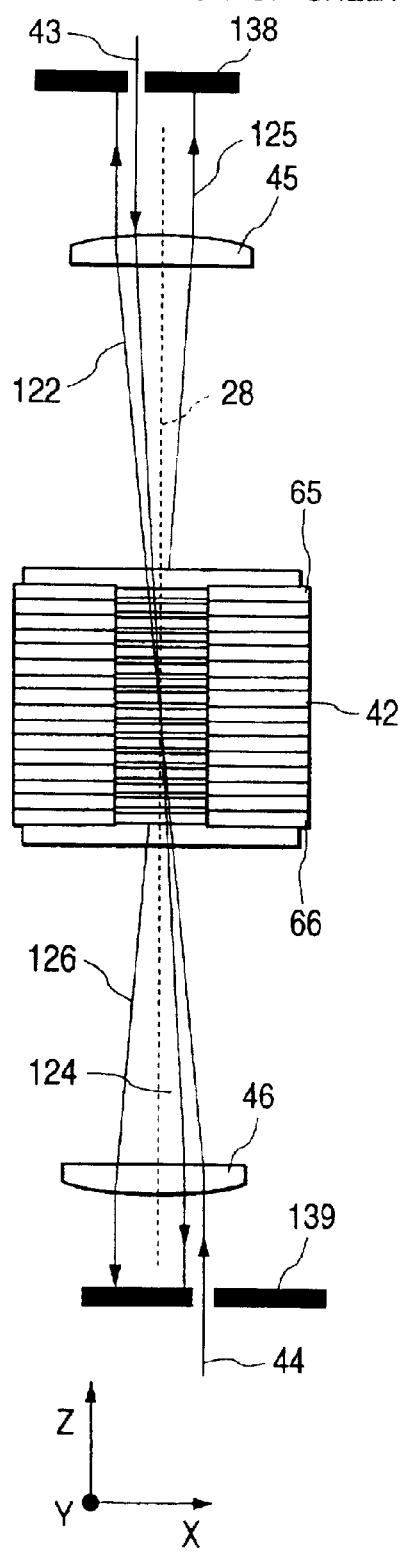
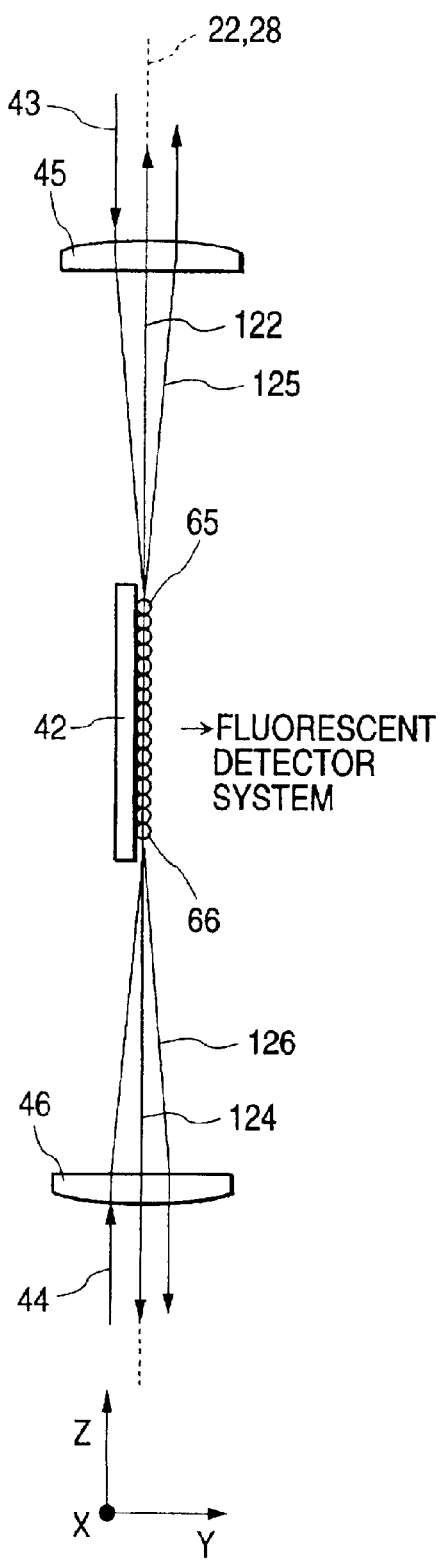

CAPILLARY ARRAY ELECTROPHORESIS APPARATUS

BACKGROUND OF THE INVENTION

Field of the Invention

The present invention relates to an electrophoresis apparatus in which specimens such as DNA and protein are separated and analyzed through electrophoresis by making use of a capillary array constituted by collecting a plurality of capillaries.

Electrophoresis which makes use of capillaries has been used for the purpose of determining, for example, base sequencing and base length of DNA. When a specimen containing DNA which is the object of measurement is injected into gel such as polyacrylamide within a glass capillary and a voltage is applied between both ends of the capillary, DNA compounds in the specimen move in the capillary and are separated depending on such as their molecular weights to form DNA bands within the capillary. Since a fluorescent coloring matter is added for the respective DNA bands, when laser beam is irradiated thereto, light is emitted therefrom, thus through reading of the emitted light by means of a fluorescent measurement means the sequencing of DNA is determined. The separation and analysis of protein are performed in a like manner to examine the structure of the protein.

One such laser beam irradiation method is as follows. In a capillary array constituted by a plurality of capillaries, a cover coating such as polyamide on the surface of the capillaries is removed to form a detection portion, laser beam is irradiated to a capillary located at one side or capillaries located at both sides in the detection portion and the laser beam irradiated in such a manner passes across the plurality of capillaries.

In the above explained conventional laser beam irradiation method, when the laser beam is irradiated from one side of the capillary array, reflection beam from the surface of the capillary array returns to a laser oscillator which causes a problem of instabilizing the laser oscillation. Further, when irradiating laser beam from both sides of the capillary array, other than the reflected beam from the surface of the capillary array, the beam transmitted through the capillary array returns to the laser oscillator which causes a problem of instabilizing the laser oscillation.

According to the present invention, at least the following three methods which resolve the problems of the returning beam and the reflected beam from the capillary array are used. In strict sense no plane faces exist in the capillary array, however, when a plurality of capillaries are aligned in parallel, the center axes of the respective capillaries are substantially aligned on a certain plane face which is called hereinbelow as "a capillary array plane face" or "an array plane face"

(1) An irradiation optical axis making incident in parallel direction with respect to the capillary array plane face is inclined in non-perpendicular direction with respect to the longitudinal direction of the capillaries. Thus, the reflected beam from the capillaries is not overlapped on the laser beam axis, thereby, no noises are introduced.

(2) An irradiation optical axis making incident in parallel direction with respect to the capillary array plane face is inclined with respect to the array plane face. In this instance, since the laser beam is irradiated from both sides of the array, when looking at one of the beam irradiation spots, the beam transmitted through the array and the incident beam align side by side.

(3) Incident angles of two laser beam optical axes irradiated from both sides of the capillary plane face which cross each other in parallel direction with respect to the capillary array plane face are differentiated from each other.

In the present invention, at least one of the above arrangements (1) through (3) is employed. In particular, through combination of above two or three arrangements the disturbance caused by the returning beam of the irradiated beam is desirably eliminated.

Accordingly, one embodiment of the present invention which resolves the above problems is to provide a capillary array electrophoresis apparatus in which laser beam is irradiated to either one or both end capillaries at both sides of a capillary array and the laser beam passes through the plurality of capillaries is characterized, in that between a laser beam source and a laser beam condensing means which is disposed on an optical axis between the capillaries and the laser beam source at the remotest position from the capillaries, an overlapping of reflected laser beam by a capillary face to which the laser beam makes incident with the incident laser beam is prevented.

The above condition is fulfilled when the optical axis of the incident laser beam is not perpendicular to the center axis of the capillaries. In some of conventional electrophoresis apparatus having a single capillary, the optical axis of the incident beam is not exactly perpendicular to the center axis of the capillary. However, the purpose of such arrangement in the electrophoresis apparatus having the single capillary is to possibly prevent direct incidence of reflected beam to a detection system by inclining the optical axis. The purpose of inclining the laser beam optical axis according to the present invention is fundamentally different from that of the above referred to conventional art. In the above conventional art, it is necessary to incline the laser beam optical axis greatly to the extent that the direct reflection beam sufficiently offsets from a condenser lens for fluorescent light. For example, when F value of a detection system is 1.4, it is necessary to give an incident angle of more than 20°. On the other hand, according to the present invention, it is enough that when the focal distance of a condenser lens is 50 mm, the inclination of the laser beam optical axis of about 1°~2° is sufficient.

Further, another embodiment of the present invention is to provide a capillary array electrophoresis apparatus in which laser beam is irradiated to both end capillaries at both sides of a capillary array and the two laser beams respectively pass through the plurality of capillaries is characterized, in that the plane face formed by the capillary array is not in parallel with the incident laser beams. When branching the laser beam and arranging the same so as to oppose coaxially each other, a problem of returning laser beam fundamentally arises. However, in the present capillary array, the beam passing the capillaries has an optical axis around a straight line defined by a crossing line of two plane faces one formed by the capillary array and the other formed by an optical axis of the beam advancing in the capillaries and the inclined incident laser beam. Accordingly, with this measure, in the capillary array of the present invention such a condition is produced that the opposing laser beams are coaxial within the capillaries, but are not coaxial in the space out of the capillaries.

Further, still another embodiment of the present invention is to provide a capillary array electrophoresis apparatus in which laser beam is irradiated to both end capillaries at both sides of a capillary array and the two laser beams respectively pass through the plurality of capillaries is characterized, in that the orthogonal projections of the two incident laser beams with respect to the plane face formed by the capillary array are not in parallel.

When the orthogonal projections of the two incident laser beams with respect to the plane face formed by the capillary array are not parallel as referred to above, the following problem may arise. Since the laser beam diameter when adding the two laser beams becomes large in comparison with when the two laser beams are coaxial, therefore, it is feared that spatial resolution in a fluorescent detection is reduced. Namely, in an electrophoresis, DNA compounds in the specimen move in the capillary and are separated depending on, for example, their molecular weights to form DNA bands within the capillary. In such an instance, it is possible that the resolution detection capability of these DNA bands is reduced. In order to avoid those possibilities, it is preferable that the centers of the two laser beams overlap each other near the center of the capillary array. When the two laser beams are arranged like this, the expansion of the laser beam diameter is minimized.

A method of realizing the arrangement of the optical axis of the laser beams as referred to above is as follows. At first, respective condenser lenses for opposing two laser beams which are designed to condense the laser beams to the capillaries are removed. Then, the opposing two laser beams are adjusted to run substantially in parallel and to be substantially perpendicular to the capillary axis. Thereafter, the condenser lenses for condensing the laser beams to the capillaries are inserted in the passages of the two laser beams. Then, the position of the condenser lenses is adjusted so that the laser beams make incident to a fluorescence detector in the capillaries.

In the above explained method of realizing the laser beam optical axis, the position of the lenses is adjusted so that the laser beams are guided to correct positions of the capillaries. Accordingly, it is preferable that a fine adjustment function for the condenser lenses is provided. With respect to the direction of the laser beam optical axis, when the focal distance of the condenser lenses is 50 mm, the positional accuracy of the lenses required for the above direction is about 1 mm, therefore, with regard to this direction no positional adjustment function is necessarily required. However, with regard to the two axes perpendicular to the laser beam optical axis, when the ratio of inner diameter/outer diameter of the capillaries is 50 $\mu m$/320 $\mu m$, a positional accuracy of about 10 $\mu m$ is required. In this instance, if a screw having a pitch of about 0.5 mm is used as a screw for adjusting the position of the condenser lenses, the requirement will be satisfied.

Further, in the method of realizing the laser beam optical axis, in order to arrange the opposing two laser beams in substantially parallel each other at a proper position, when a set of plate shape members, in each of which apertures having a comparable diameter as the diameter of the laser beams are formed, are used at respective positions where two laser beams substantially being in parallel pass as a laser beam optical axis adjustment jig, the adjustment can be performed easily.

In the present invention, since the laser beam optical axis is not perpendicular to the capillary axis, when the capillaries are disposed horizontally, the laser beam optical axis can not direct in vertical direction. As a multi-capillary detection means, a two dimensional CCD (Charge Coupled Device) camera is frequently used. In such instance, one dimension among two dimensions of the CCD camera is aligned along the arrangement direction of the capillaries as an axis for detecting signals from the respective capillaries and the other dimensional axis is aligned along a wave length dispersion direction of fluorescent light emitted from the respective capillaries. Namely, the latter direction is determined as the direction for dispersing the emitted light from the single capillary by making use of a grating and a prism. In the present invention, although the capillary axis and the laser beam optical axis are not substantially perpendicular, in an electrophoresis apparatus which makes use of a CCD in a fluorescent detection means, it is preferable that a pixel grid in the CCD is parallel to the optical axis of the laser beam passing through the capillaries rather than substantially parallel to the capillary axis in view of taking-in of data from the CCD.

Further, in an electrophoresis apparatus, including a wave length dispersion means such as a grating and a prism in a fluorescent detection means according to the present invention, it is preferable that the wave length dispersion direction of the wave length dispersion means and the optical axis of the laser beam passing the capillaries are substantially perpendicular to each other in view of taking-in of data from the CCD.

BRIEF DESCRIPTION OF THE DRAWINGS

FIG. 4A is a skeleton diagram of a fluorescent detection system according to the present invention, and FIG. 4B is a diagram for showing rotation angles of a capillary array, laser beam optical axis, grating and CCD in the detection system in FIG. 4A;

FIGS. 10A through 10D are diagrams for explaining a method of adjusting laser beam optical axes in non-coaxial;

FIGS. 13A through 13D show an adjusting method of laser beam optical axes according to another embodiment of the present invention;

FIG. 4C shows a light intensity distribution on the plane of the pin hole plate;

FIGS. 15A through 15D show an adjustment method of laser beam optical axes according to still another embodiment of the present invention;

DETAILED DESCRIPTION OF THE PREFERRED EMBODIMENTS

First Embodiment

Figure 2:
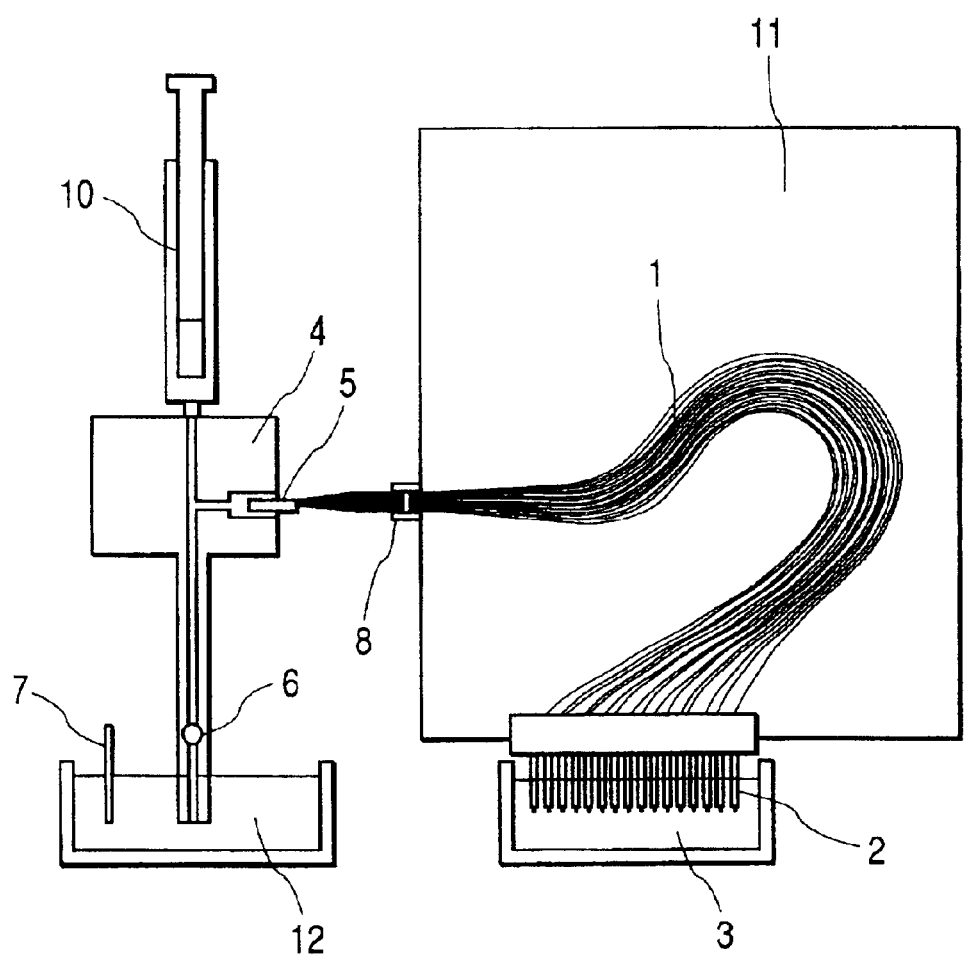
FIG. 2 is a schematic diagram of a major portion of an electrophoresis apparatus according to the present invention.

FIG. 2 shows an overview of an electrophoresis apparatus according to the present invention. At one end of a capillary array 1 an electrode (a specimen introduction terminal) 2 is formed so as to permit application of a negative voltage. When injecting DNA, the cathode 2 immersed into a solution containing DNA sample and further when performing electrophoresis of the injected sample, the cathode 2 is immersed into a butter solution 3 and a predetermined voltage is applied thereto. At the other end of the capillary 1 a connection portion 5 is formed which leads to a gel block 4 functioning as a means for injecting gel serving as an electrophoresis medium into capillaries. When charging gel serving as an electrophoresis medium into the capillaries, a valve 6 is closed and a syringe 10 is pressed down, thereby, the gel within the syringe 10 is injected into the capillary array 1, when performing an electrophoresis, the valve 6 is opened and a predetermined voltage is applied between the cathode 3 immersed in the buffer and an earth electrode 7 immersed in another buffer 12. The capillary array 1 is kept at a constant temperature by means of a gas circulation type thermostatic oven 11.

Figure 3A:
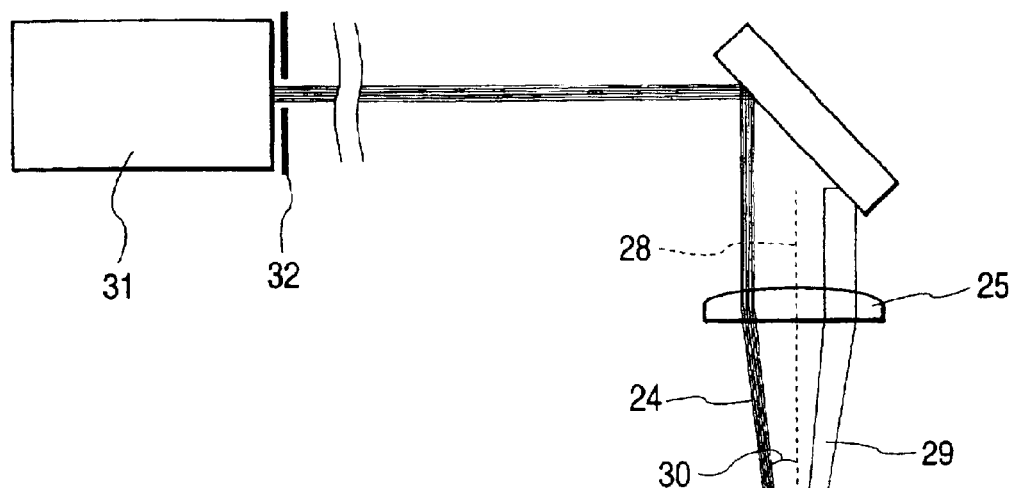
FIG. 3A is a schematic diagram showing a major portion in another embodiment of an electrophoresis apparatus according to the present invention.
Figure 3B:
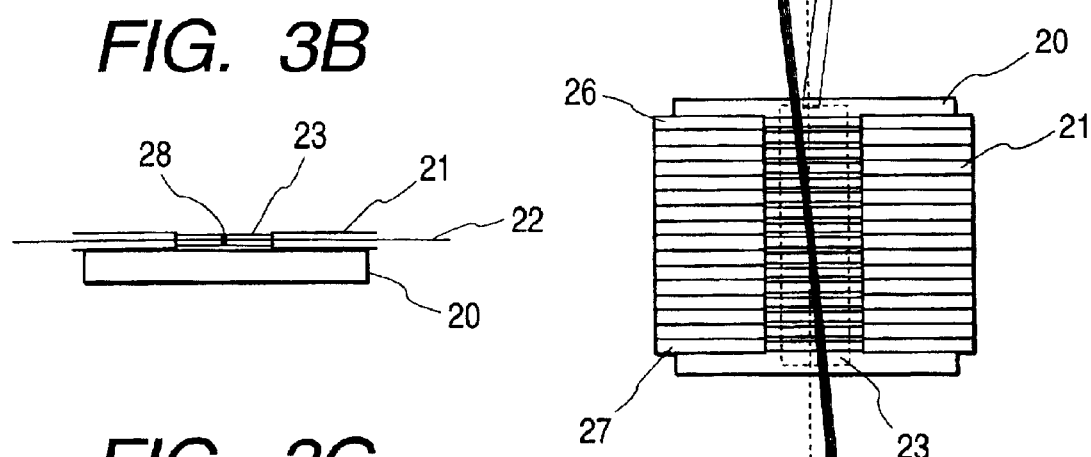
FIG. 3B is a top side view of an irradiation and detection portion in a capillary array in FIG. 3A
Figure 3C:
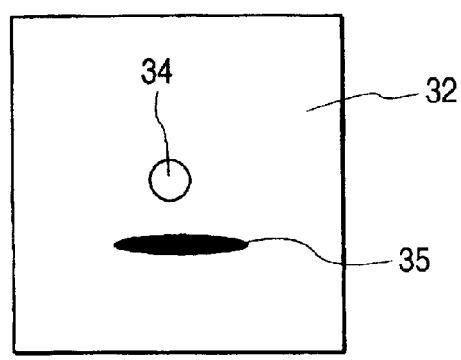
FIG. 3C is a plane view of a pin hole plate which is attached at an emission port of a laser beam source in FIG. 3A.

FIGS. 3A through 3C show skeleton diagrams near a detection portion (8 in FIG. 2) of a capillary array and a laser beam introduction route. Since elements such as a shutter and a filter used for laser beam are well known in the field concerned and are not a direct object of the present invention, the illustration thereof is omitted for the sake of simplicity. FIG. 3A is a schematic front view of a major portion of an electrophoresis apparatus according to the present embodiment, FIG. 3B is an upper side view of the detection portion of the capillary array and FIG. 3C is a plane view of a pin hole plate which is attached at an emission port of a laser beam source. A capillary array is formed by arranging 16 pieces of capillaries 21 on an array stand 20 and by securing the same thereon. Hereinafter, a plane face formed by the center axes of 16 pieces of capillaries 21 on the array stand 20 and an imaginary plane face formed by extending the former plane face over the entire space are called an array face 22. Further, an imaginary straight line which is in the array face is perpendicular to 16 pieces of capillary axes and passes through the center of the detection portion is called a standard optical axis 28 (see FIG. 3A). The capillaries are made of a quartz glass tube covered by a polymer thin film, however, at the detection portion the polymer covering is removed and the quartz glass is exposed. The inner diameter/outer diameter ratio of the quartz glass tube is 50/320 $\mu$m and the outer diameter of the capillary including the polymer thin film is 363 $\mu$m. The pitch of the capillaries is 363 $\mu$m same as the capillary outer diameter and the width of the array is 363 $\mu$m×16=5.8 mm.

After irradiating laser beam 24 to a fluorescent detection portion 23 in the capillary array from one side face of the array and observing fluorescent light emitted from the detection portion 23, DNA is detected. The laser beam 24 is condensed by a laser condenser lens 25 (f=50 mm). A capillary which is positioned at one end of the array and to which the laser beam 24 firstly introduced is identified as a first capillary 26 hereinbelow. The distance between the laser beam condenser lens 25 and the first capillary 26 is 50 mm, and the laser beam 24 introduced into the first capillary 26 successively propagates the adjacent capillaries and crosses through the 16 pieces of capillaries.

Reflection of the incident laser beam is caused at an interface of air/capillary outer wall and at a capillary inner wall/gel interface, in particular, since a refractive index difference at the interface of air/capillary outer wall is large, the reflection light intensity thereat becomes large. Since there exists two interfaces of air/capillary outer wall for every capillary, reflection is caused from 32 interfaces of air/capillary outer wall of 16 pieces of capillaries.

In the present embodiment, as illustrated in FIG. 3A, the laser beam 24 makes incident to the first capillary 26 with an inclined angle 30 of about 2° with respect to a perpendicular line 28 to 16 pieces of capillary axes. The laser beam 24 is on the array face 22 and makes incident inclinedly to the first capillary 26 on the array face 22. As the result of the inclined incidence of the laser beam 24, reflection light 29 from the capillary offsets from the incident laser beam 24. After passing the condenser lens 25, the reflection light 29 runs substantially in parallel with the incident laser beam 24. The distance between the incident laser beam 24 and the reflection light 29 was about 4 mm. At the laser beam emission port of a laser beam source 31 a pin hole plate 32 having a pin hole 34 of 1.4 mm diameter is attached and the center of the pin hole was matched with the center of the laser beam 24. A spot 35 of the reflection light 29 on the pin hole plate 32 is illustrated in FIG. 3C which shows that the reflection light 29 is interrupted by the pin hole plate 32 and is prevented from returning to the laser beam source 31. With the above measure, a stable laser oscillation can be obtained.

Embodiment 2

Figure 17:
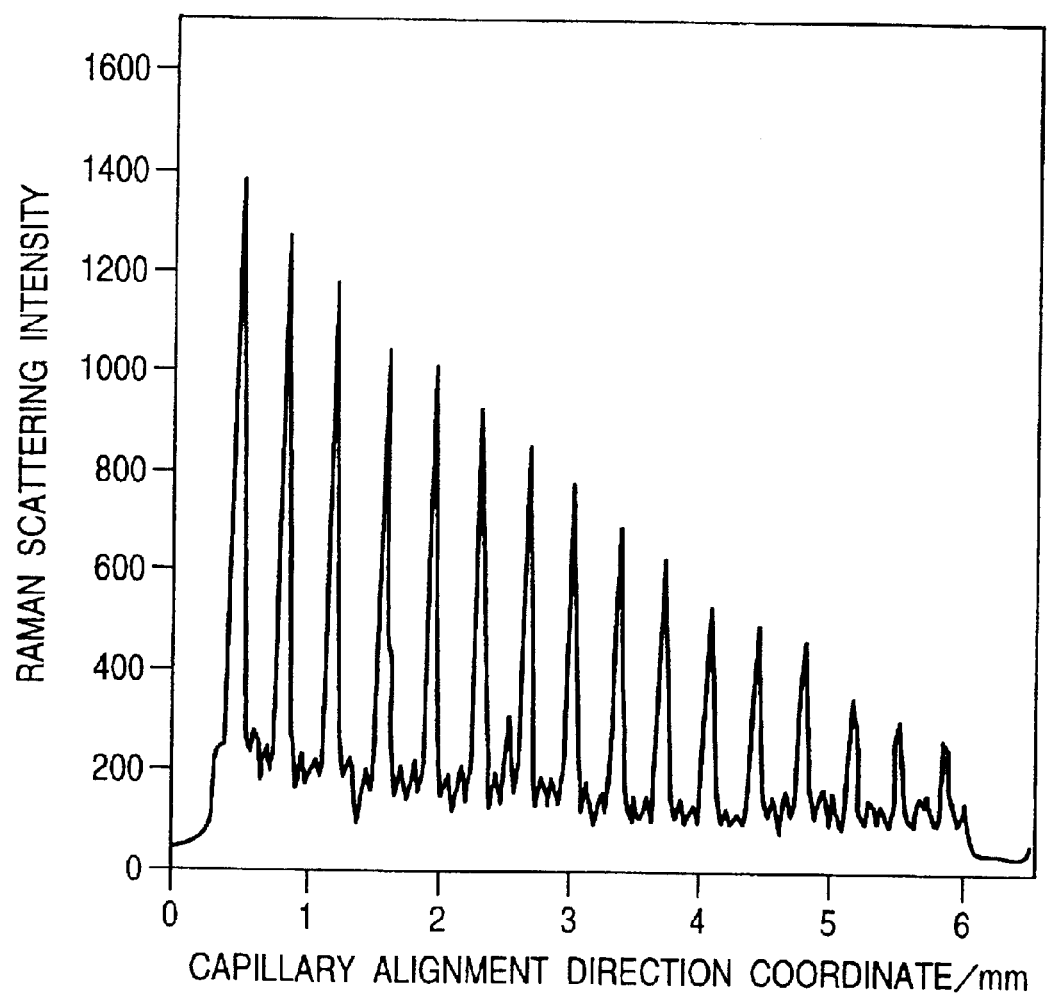
FIG. 17 shows a signal intensity distribution in the first embodiment as shown in FIGS. 3A through 3C according to the present invention.

FIG. 17 shows a signal intensity distribution for the 16 pieces of capillaries in the embodiment 1 above. As will be seen from FIG. 17, when the laser beam is introduced only at one side face of the capillary array, variations of signal intensities among the 16 pieces of capillaries are enlarged. According to the present embodiment, the laser beams are introduced from both side faces of the capillary array, thereby, the dispersion of the signal intensities from the 16 pieces of capillaries is reduced.

Figure 1:
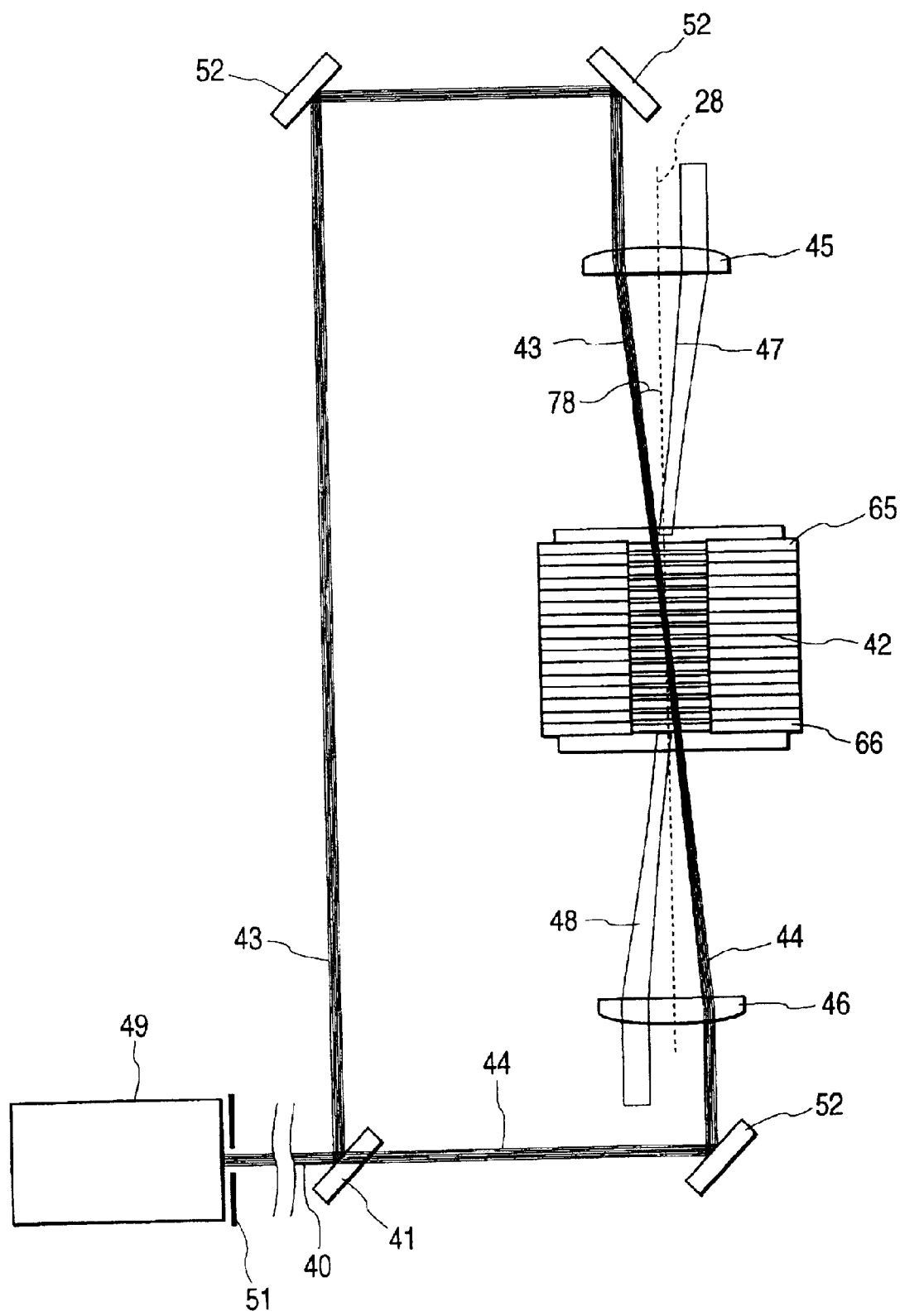
FIG. 1 is a schematic diagram showing an arrangement of an irradiation and detection system and other major portions in an embodiment of an electrophoresis apparatus according to the present invention.

FIG. 1 shows a skeleton diagram of embodiment 2 according to the present invention, in which only the vicinity of the detection portion of the capillary array and the laser beam introduction route thereof are illustrated and the illustration of the elements such as a shutter and a filter used for the laser beam is omitted. The structure of the capillary array in embodiment 2 is identical to that in embodiment 1. Further, the name of parts and the definition of terms in the present embodiment are the same as those in embodiment 1 if not otherwise defined. A laser beam 40 is equally divided into two by a half mirror 41 and these two laser beams are irradiated to a capillary array from both side faces thereof via mirrors 52. The reflection light by the half mirror 41 is identified as laser beam 43 and the transmitted light is identified as laser beam 44. The condenser lens for the laser beam 43 is identified as a condenser lens 45 and the condenser lens for the laser beam 44 is identified as a condenser lens 46.

A capillary positioned at one end of the array and to which the laser beam 43 is first introduced is identified as first capillary 65 hereinbelow and another capillary to which the laser beam 44 is first introduced is identified as $16^{th}$ capillary 66 hereinbelow. The optical axis layout of the laser beam 43 is the same as that in the embodiment 1. Further, the optical axis layout of the laser beam 44 is in symmetry to that of the laser beam 43 with respect to the capillary array. The optical axes of the laser beams 43 and 44 are adjusted in such a manner that the laser beams 43 and 44 are coaxial and one of the laser beams which passes through the capillaries further passes coaxially through the optical axis of the other incident laser beam and returns to the laser beam source 49. Respective reflection lights 47 and 48 from the capillaries of the laser beams 43 and 44 run in non coaxial manner with respect to the two laser beams 43 and 44 as illustrated in FIG. 1. Like the embodiment 1, at the laser beam emission port of the laser beam source 49 a pin hole plate 51 having a pin hole of a 1.4 mm diameter is attached so as to prevent the reflection lights from returning to the laser beam source or the laser oscillator 49. Although the transmitted lights through the capillaries return to the emission port of the laser beam source 49, the returning of the reflection lights to the laser beam source 49 is prevented, thereby, a comparatively stable laser oscillation can be obtained.

FIG. 4A shows a skeleton diagram of a fluorescent detection system according to the present embodiment. An emission light 53 from the capillaries 42 is converted into a parallel light by an emission light condenser lens 54 of f=1.4 and the parallel emission light is introduced to a transmission type grating 55. Lights 56 and 57 spectrumed by the grating 55 are focused on a two dimension CCD 59 by an image formation lens 58. The wavelength dispersion direction by the grating 55 is substantially perpendicular with respect to the laser beam optical axis. Thereby, among two orthogonally crossing axes on the two dimension CCD 59, one of the axes represents a spatial coordinate in the alignment direction of the 16 pieces of the capillaries and the other axis represents emission light spectrums of the respective capillaries.

Further, in the area surrounded by a broken line 60 in FIG. 4B the capillary array 42 and the laser beam optical axis 61 and rotation angles of the grating 55 and CCD 59 are illustrated in skeleton when seen from a direction directing from the capillary array 42 to the grating. The grating and the CCD are arranged in such a manner that the grids of the grating and the grids of pixels in the CCD align not in perpendicular to the capillary axes but substantially in parallel with the laser optical axis. Thereby, signals having a same wavelength from the respective capillaries align on a same longitudinal row 62 on the CCD pixels and emission light spectrums from each capillary align on a same lateral row 63 of the CCD pixels. Such relationship between the image and the pixels is advantages when performing a binning process on an analysis of the image.

Figure 5A:
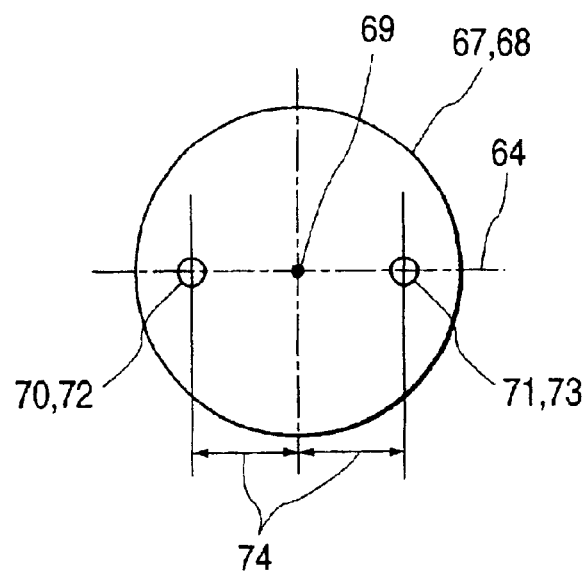
FIGS. 5A and 5B are plane views of a pair of pin hole plates used in the present invention.
Figure 5B:
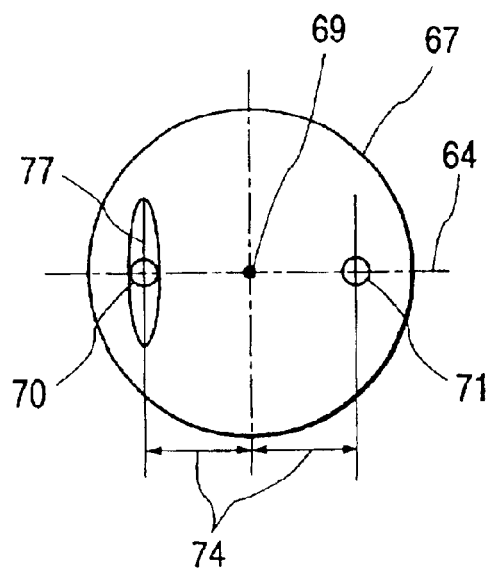

Laying out the optical axis according to the present embodiment is realized by making use of a set of the pin hole plates as shown in FIG. 5A. At first, the laser beam condenser lenses 45 and 46 are removed from the electrophoresis apparatus, then pin hole plates 67 and 68 in which pin holes are formed as illustrated in FIG. 5A are disposed at the positions where the laser beam condenser lenses 45 and 46 were disposed. Hereinafter, a crossing line between the pin hole plate and the array face is called as an array reference line 64 and a crossing point of a straight line which is perpendicular to the pin hole plate and passes through the center position of detection portion for the first capillary with the pin hole plate is called a pin hole reference point 69.

The position of the pin holes in the pin hole plates 67 and 68 is determined as follows depending on an incident angle of the laser beam to the capillaries to be set. There are provided two pin holes for each pin hole plate, in that pin holes 70 and 71 for the pin hole plate 67 and pin holes 72 and 73 for the pin hole plate 68, the centers of these pin holes are placed on the array reference line 64 and a midpoint of the pin holes located at the pin hole reference point 69. When assuming that the distance 74 from the pin hole reference point 69 to the center of the pin hole is X, a laser beam incident angle 78 to the capillaries is T1 and (distance between the condenser lens 45 and the first capillary 65)+ (width of the capillary array)/2 is as L1, the following equation stands;

$X = L1 \times \tan T1$

Namely, in the present embodiment, while selecting L1=52.9 mm wherein the distance between the condenser lens 45 and the first capillary 65 is 50 mm and the width of the capillary array is 5.8 mm and T1=2.1°, X is determined as 1.9 mm.

Figure 6A:
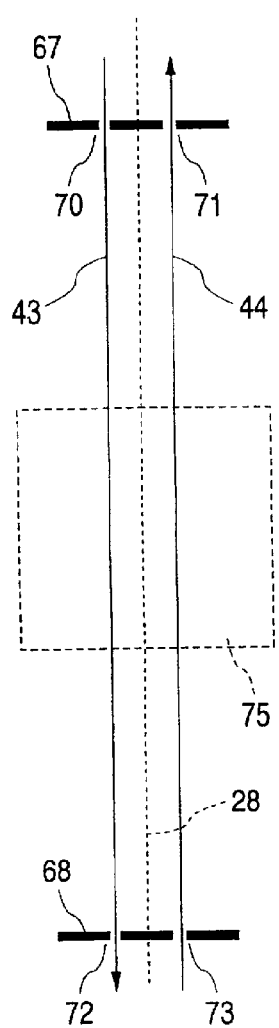
FIG. 6A shows a method of adjusting a laser beam optical axis by pin hole plates.
Figure 6B:
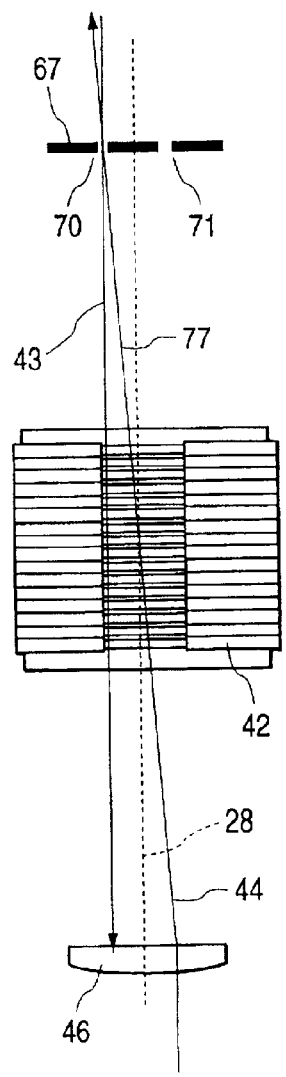
FIG. 6B shows a change of optical axis by a combination of a pin hole plate and a condenser lens and FIG. 6C shows a change of optical axis when two pieces of pin hole plates are replaced by two condenser lenses.

After removing the capillary array from a capillary array attachment position 75, the laser beam optical axis is adjusted in such a manner that the laser beam 43 passes through the pin holes 70 and 72 respectively in the pin hole plates 67 and 68, the laser beam 44 passes through the pin holes 71 and 73 and the two laser beams run substantially in parallel as illustrated in FIG. 6A. After removing the pin hole plate 68, the condenser lens 46 and the capillary array 42 into which an electrophoresis medium is injected are disposed at respective installation positions as illustrated in FIG. 6B. In this instance, the position of the condenser lens 46 is determined as follows.

X, Y and Z axes are assumed as illustrated in FIG. 6B. Z axis direction is determined so that the distance between the condenser lens 46 and the 16th capillary 66 gives 50 mm. With regard to Y direction the position of the condenser lens 46 is adjusted so that transmission light intensity when the laser beam 44 transmits the capillary array is maximized. Through the displacement of the position of the condenser lens 46 in Y axis direction the irradiation position of the laser beam 44 onto the 16th capillary displaces in Y axis direction.

In the present embodiment, a lens position adjustment function of about 10 µm is required. With regard to X axis direction, the center of a transmission light 77 when the laser beam 44 transmits the capillary array is adjusted so as to come to the center of the pin hole 70 in the pin hole plate 67.

Figure 6C:
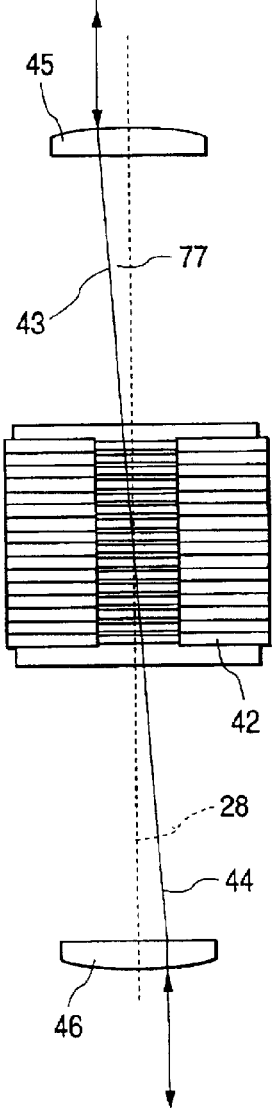

Thereafter, the pin hole plate 67 is removed and the condenser lens 45 is set as illustrated in FIG. 6C. With regard to Y and Z axes, like adjustment as performed in connection with the condenser lens 46 is performed. With regard to X axis, the position thereof is determined in such a manner that the two irradiation laser beams overlap each other at 8th capillary counting from the first capillary. In this instance it is sufficient if the adjustment is performed in such a manner that after observing Raman scattering of narrow spectral width with the CCD, the Raman band due to the laser beam 43 overlaps with the Raman band due to the laser beam 44. With the above sequence the optical axis alignment according to the present embodiment can be realized.

Further, a reflection light of the incident laser beam which is reflected only once from the surface of the capillaries is incident on a lens in the fluorescent detection system, and such direct reflection light is eliminated by an optical filter.

Embodiment 3

Figure 9A:
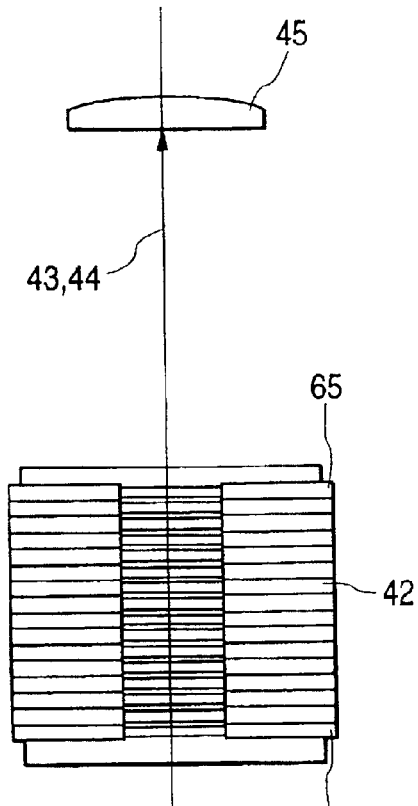
FIGS. 9A and 9B are diagrams for explaining an adjusting method of laser beam optical axes by making use of a single condenser lens.
Figure 9B:
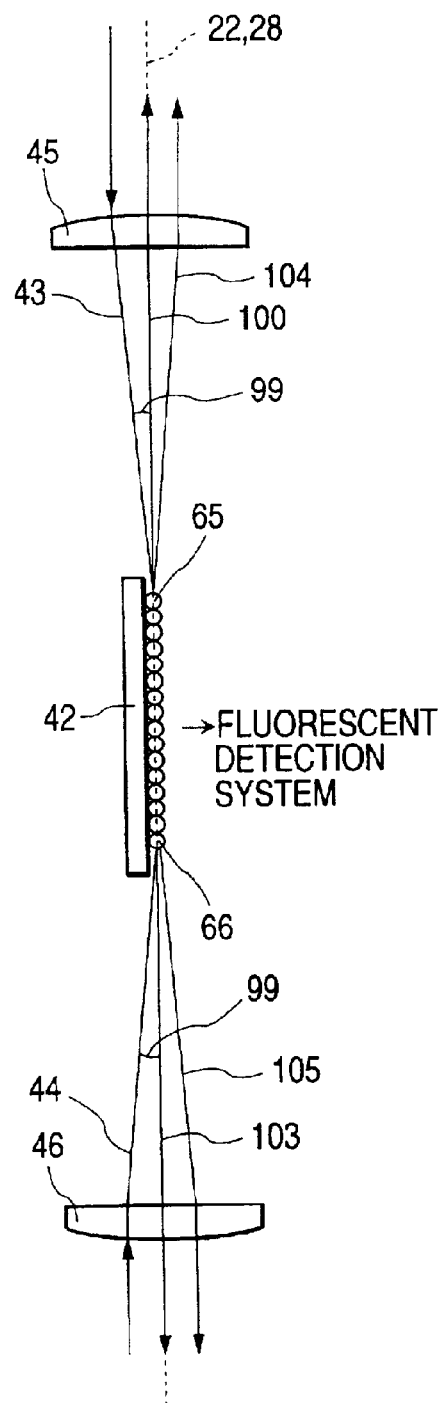

FIGS. 9A and 9B show skeleton diagrams of embodiment 3 according to the present invention. FIG. 9A is a front view thereof and FIG. 9B is a side view thereof, in which only the vicinity of the detection portion of the capillary array and the laser beam introduction route thereof are illustrated and the illustration of the elements such as a shutter and a filter used for the laser beam is omitted. In the present embodiment, no incident laser beams run on the array face 22 and the laser beam makes incident with an angle 99 of about 2° with respect to the array face 22. The structure of the capillary array in embodiment 3 is identical to that in embodiment 2. Further, the names of parts and the definition of terms in the present embodiment are the same as those in embodiments 1 and 2 if not otherwise defined.

Figure 7A:
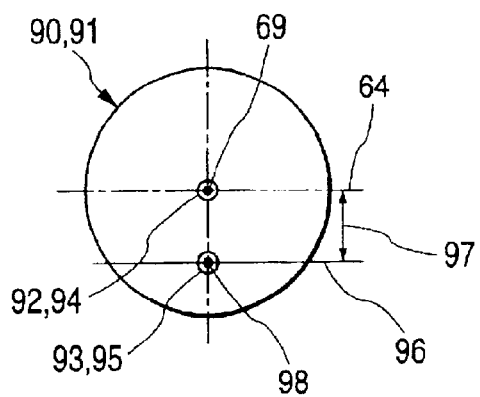
FIGS. 7A and 7B are plane views showing respective shapes of pin hole plates and FIGS. 7C and 7D show light intensity distributions on broken lines in FIGS. 7A and 7B.
Figure 7B:
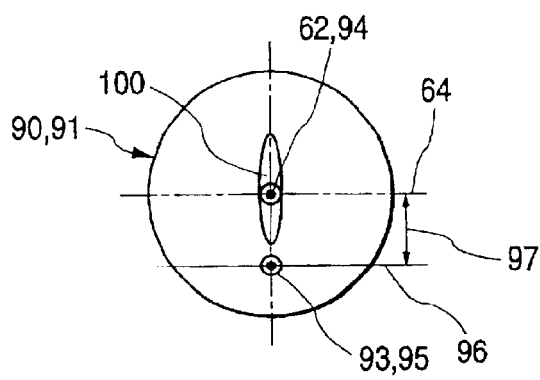

In order to realize such optical axis layout an optical axis adjustment is performed as follows by making use of pin hole plates as illustrated in FIG. 7A. At first, the two condenser lenses 45 and 46 are removed from the electrophoresis apparatus and pin hole plates 90 and 91 in which pin holes are formed as illustrated in FIG. 7A are disposed at positions where the laser beam condenser lenses 45 and 46 were respectively disposed.

The position of the pin holes in the pin hole plates is determined as follows depending on an incident angle of the laser beam to the capillaries to be set. There are provided two pin holes for each pin hole plate, in that pin holes 92 and 93 for the pin hole plate 90 and pin holes 94 and 95 for the pin hole plate 91. A straight line which is away from the array reference line 64 by a distance 97 of Y and is substantially in parallel with the array reference line 64 and in opposite side from the grating in the detection system with respect to the array reference line 64 is identified as an elevation angle line 96 hereinbelow. Further, a crossing point of a perpendicular line of the array reference line 64 passing through the pin hole reference point 69 with the elevation angle line 96 is identified as an elevation angle line reference point 98 hereinbelow. An adjustment is performed in such a manner that the center of the pin hole 92 comes to the pin hole reference point 69 and the center of the pin hole 93 comes to the elevation angle line reference point 98.

When assuming that an angle formed by a plane defined by the center of the pin hole 92 and the center axis of the first capillary 65 and the array face is T2, and the distance between the condenser lens and the first capillary is L2, an adjustment is performed in such a manner that the following equation stands;

$$Y = L2 \times \tan T2$$

Namely, in the present embodiment, while selecting L2=50 mm and T2=2.2°, Y is determined as 1.9 mm. The pin holes 94 and 95 in the pin hole plate 91 are set in the same manner.

Figure 8A:
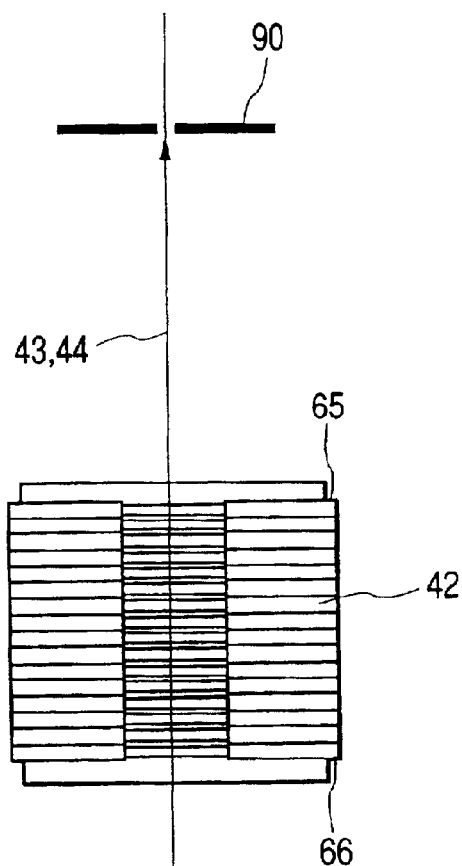
FIGS. 8A and 8B show a method of adjusting laser beam optical axes to align in coaxial by making use of a pair of pin hole plates.
Figure 8B:
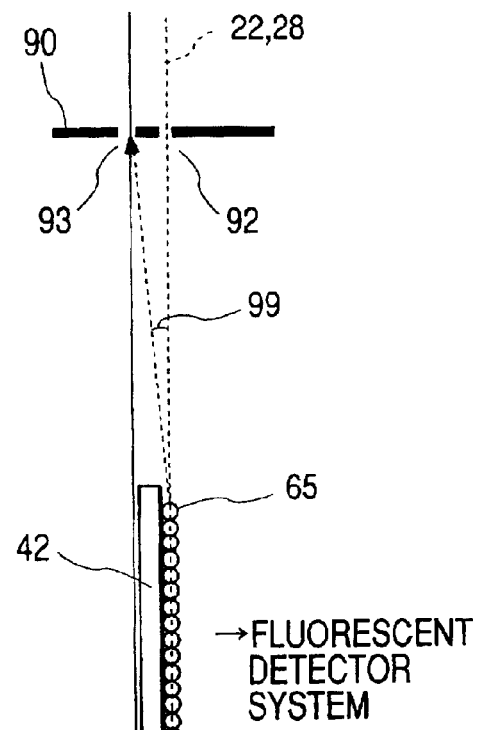

As illustrated in FIGS. 8A and 8B, the laser beam optical axis is adjusted in such a manner that the laser beams 43 and 44 respectively pass the pin holes 93 and 95 in the respective pin hole plates set at two locations and the two laser beams run in coaxial. FIG. 8A shows a front view thereof and FIG. 8B shows the side view thereof. At first, the pin hole plate 91 is removed and the condenser lens 46 is set. In this instance, the position of the lens is determined as follows. X, Y and Z axes are assumed as illustrated in FIGS. 8A and 8B. With regard to Y and Z axes, like optimization as in the embodiment 2 is performed. With regard to X axis direction, an adjustment is performed so that the center of transmission light 100 when the laser beam 44 transmits through the capillary array comes to the center of the pin hole 92 in the pin hole plate 90 as illustrated in FIG. 8B. Then, after removing the pin hole plate 90, the condenser lens 45 is set. With regard to X, Y and Z axes, the optimization of the lens position is performed in the like manner as in the embodiment 2. With the above sequence and by making use of the pin hole plates and setting the distances X and Y properly, the incident angle of the laser beam to the capillaries can be set as desired.

Figure 7C:
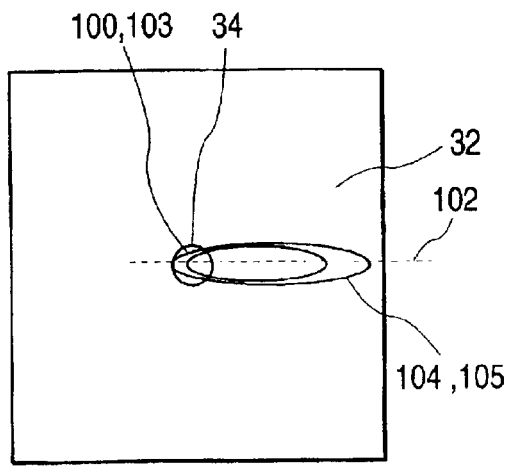
Figure 7D:
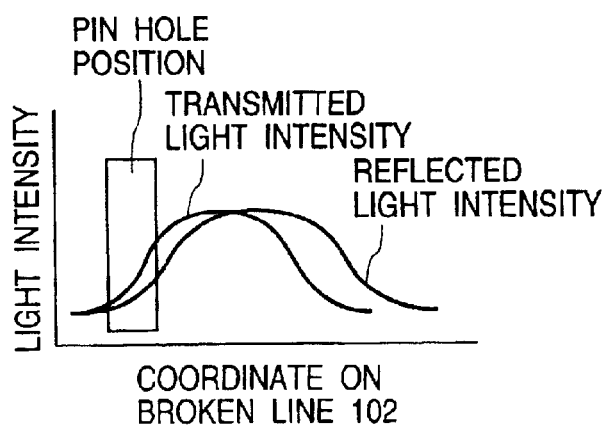

Further, like the embodiment 1, at the laser beam emission port of the laser beam source a pin hole plate 32 having a pin hole 34 of 1.4 mm diameter is disposed, light spots of the transmission lights 100 and 103 respectively corresponding to the laser beams 44 and 43 which have returned to the laser beam source after transmitting the capillaries are observed as illustrated in FIG. 7G. Likely, light spots of reflected lights 104 and 105 from the capillaries are observed on the pinhole plates 32 as illustrated in FIG. 7C. As will be seen from the light intensity distribution on a broken line 102 in FIG. 7C as illustrated in FIG. 7D, according to the present embodiment, a returning of the highest intensity components of the transmission light through the capillaries to the laser beam source is prevented. With the present embodiment, the intensity of the returning light is reduced, thereby, an instability of the laser oscillation is prevented.

In the present invention, a combination of embodiments 2 and 3 can be provided, in that at first the two laser beam condenser lenses are removed from the electrophoresis apparatus and likely the pin hole plates are disposed at the positions where the respective laser beam condenser lenses were disposed.

The position of the pin holes in the pin hole plates 67 and 68 is determined as follows depending on an incident angle of the laser beam to the capillaries to be set. There are provided four pin holes for each pin hole plate. The centers of the pin holes are placed on a straight line which is away from the array reference line by a certain distance and in parallel therewith (and which is placed in the opposite side from the grating in the detection system with respect the array reference line and which is called as an elevation angle line hereinbelow), and a midpoint of the two pin holes is determined to match with a crossing point (which is called hereinbelow as an elevation angle line reference point) defined by a perpendicular line to the array reference line and passing the pin hole reference position and the elevation angle line. Further, crossing points defined by perpendicular lines to the elevation angle line and passing the respective pin holes and the array reference line are determined. Thereafter, while assuming that the distance from the elevation angle reference point to the center of pin hole is as X, an angle defined by the orthogonal projection of the incident laser beam on the array face and the capillary array is as T1, an angle defined by a plane face formed by the elevation angle reference point and the center axis of the first capillary and the array face is as T2 and the distance between the condenser lens and the first capillary is as L2, an adjustment is performed so that the following equations stand;

$$X = L1 \times \tan T1$$

$$Y = L2 \times \tan T2$$

Namely, in the present embodiment including the above modification, when selecting L1=53 mm, L2=50 mm, T1=2.1° and T2=2.2°, X is determined as 1.9 mm and Y is determined as 1.9 mm.

Embodiment 4

FIGS. 10A through 10D show skeleton diagrams of embodiment 4 according to the present invention, in which only the vicinity of the detection portion of the capillary array and the laser beam introduction route thereof are illustrated and the illustration of the elements such as a shutter and a filter used for the laser beam is omitted. FIG. 10A shows a method of adjusting the laser beam axis with two pin hole plates, FIG. 10B shows a state when one of the pin hole plates is replaced by a condenser lens, FIG. 10C is a front view showing a state when two condenser lenses are inserted and FIG. 10D is a side view of FIG. 10C. Like the embodiment 2, the two laser beams 43 and 44 are on the array face 22. However, unlike the embodiment 2 these two laser beams are not in coaxial but are offset by 0.96°. All of the center axes of transmitted light 124 after the incident laser beam 43 transmits through the capillaries, transmitted light 122 after the laser beam 44 transmits through the capillaries, reflection light 125 of the laser beam 43 by the capillaries and reflection light 126 of the laser beam 44 by the capillaries are designed so as not to be in coaxial with the incident laser beams 43 and 44. These incident laser beams, the transmitted lights and reflection lights run substantially in parallel at the outer sides of the condenser lenses with respect to the capillary array. Further, structure of the capillary array in the present embodiment is identical as that in the embodiment 2. Still further, the name of parts and the definition of terms in the present embodiment are the same as those in the embodiments 1, 2 and 3 if not otherwise defined.

Figure 11A:
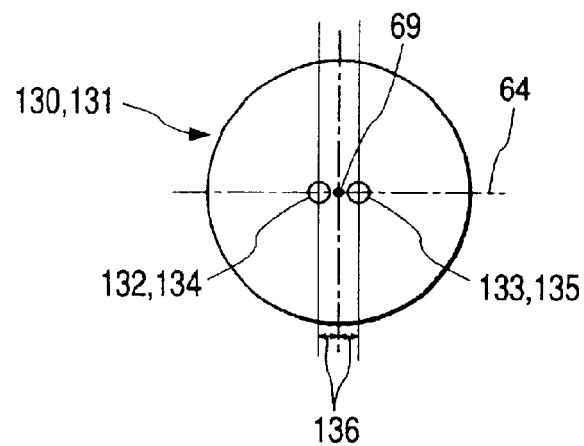
FIGS. 11A and 11B are plane views showing structures of pin hole plates.

In order to realize such optical axis layout an optical axis adjustment is performed as follows by making use of pin hole plates as illustrated in FIG. 11A. At first, the two condenser lenses 45 and 46 are removed from the electrophoresis apparatus and pin hole plates 130 and 131 in which pin holes are formed as illustrated in FIG. 11A are disposed at positions where the laser beam condenser lenses 45 and 46 were respectively disposed.

The position of the pin holes in the pin hole plates is determined as follows depending on the offset angle of the two laser beams to be set. There are provided two pin holes for each pin hole plate, in that pin holes 132 and 133 for the pin hole plate 130 and pin holes 134 and 135 for the pin hole plate 131, the centers of these pin holes are placed on the array reference line 64 and a midpoint of the two pin holes is determined to come to the pin hole reference point 69. When assuming that distance 136 from the pin hole reference point 69 to the center of the pin holes is as dX, the offset angle 137 of the two laser beams is as 2×dT1 and (distance between the condenser lens 45 and the first capillary 65)+ (the width of the capillary array)/2 is as L1, an adjustment is performed so that the following equation stands;

$$dX = L1 \times \tan(dT1)$$

Namely, in the present embodiment when selecting L1=52.9 mm (the distance between the condenser lens 45 and the first capillary 65 is 50 mm and the width of the capillary array is 5.9 mm) and dT1=0.86°, dX is determined as 0.4 mm. Further, the diameter of the respective pin holes is determined as 0.5 mm.

After removing the capillary array from a capillary array attachment position 75, the laser beam optical axis is adjusted in such a manner that both the laser beams 43 and 44 respectively pass the pin holes 93 and 95 in the respective pin hole plates set at two locations and the two laser beams run in coaxial as illustrated in FIG. 10A. After removing the pin hole plate 131, the condenser lens 46 and the capillary array 42 into which an electrophoresis medium is injected are disposed at respective installation positions as illustrated in FIG. 10B. In this instance, the position of the condenser lens 46 is determined as follows.

X, Y and Z axes are assumed as illustrated in FIGS. 10A through 10D. With regard to Y and Z axes, like optimization as in the embodiment 2 is performed.

Figure 11B:
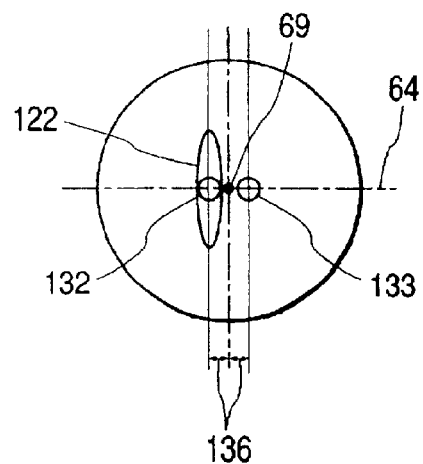

With regard to X axis direction, an adjustment is performed so that the center of transmission light 122 when the laser beam 44 transmits through the capillary array comes to the center of the pin hole 132 in the pin hole plate 130 as illustrated in FIG. 11B. Then, after removing the pin hole plate 130, the condenser lens 45 is set. With regard to X, Y and Z axes, the optimization of the lens position is performed in the like manner as in the embodiment 2. With the above sequence and by making use of the pin hole plates in which dX is properly set, the offset angle to the two laser beams can be set as desired.

Figure 11C:
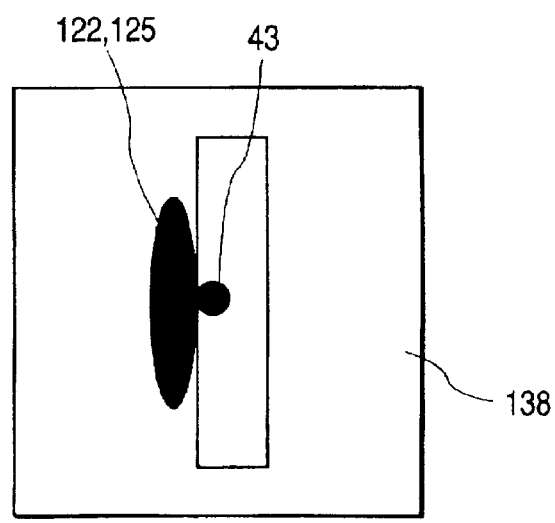
FIG. 11C a diagram showing a light intensity distribution on the pin hole plate.

As illustrated in FIG. 10C, slits 138 and 139 each having a width of 3 mm are attached at two positions in the opposite sides from the capillaries with respect to the lenses. On the slit 138 spots of the transmitted light 122 and the reflection light 125 are observed as illustrated in FIG. 11C. The slit 138 is disposed so as to transmits the incident laser beam 43 but to interrupt the transmitted light 122 and the reflection light 125. The slit 139 is likely disposed so as to transmit the incident laser beam 44 but to interrupt the transmitted light 124 and the reflection light 126. Thus, the intensity of returning light is reduced and thereby instability of the laser oscillation is prevented.

Further, at the outer side of the laser beam condenser lenses with respect to the capillary array, since incident laser beams, the transmitted lights and the reflection lights run substantially in parallel, the slits can be inserted at any positions in the outer side of the laser beam condenser lenses. In the present embodiment, the adjustment of the slit position was easy near the laser beam condenser lenses in comparison with at the emission port of the laser beam source. Therefore, an advantage is obtained with the present embodiment that the returning light intensity can be reduced easily.

Figure 12A:
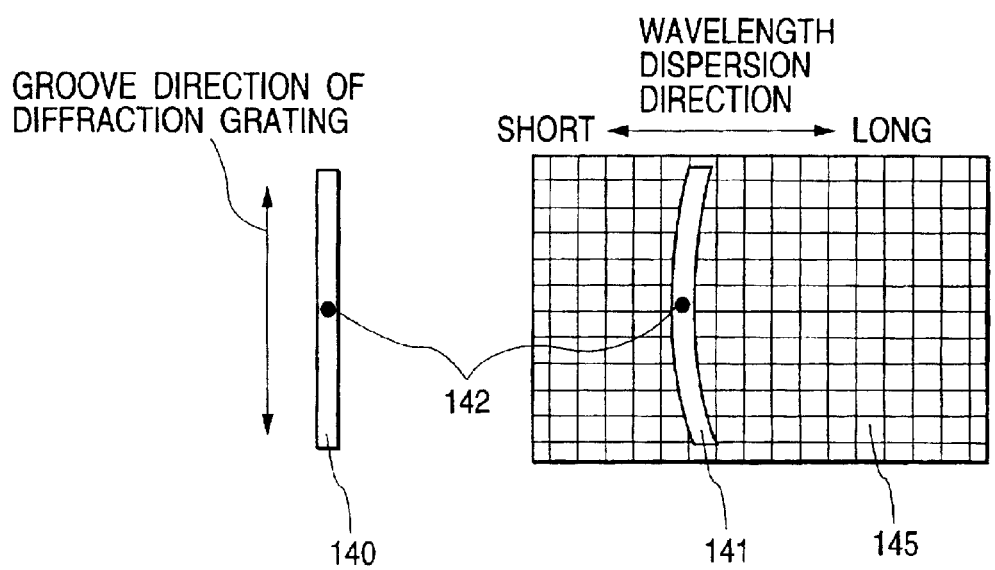
FIG. 12A shows an image formed on CCDs of a light-emitting substance that is parallel to grooves in a grating and FIG. 12B is a diagram showing in skeleton of a light intensity distribution of an incident laser beam on capillary array.
Figure 12B:
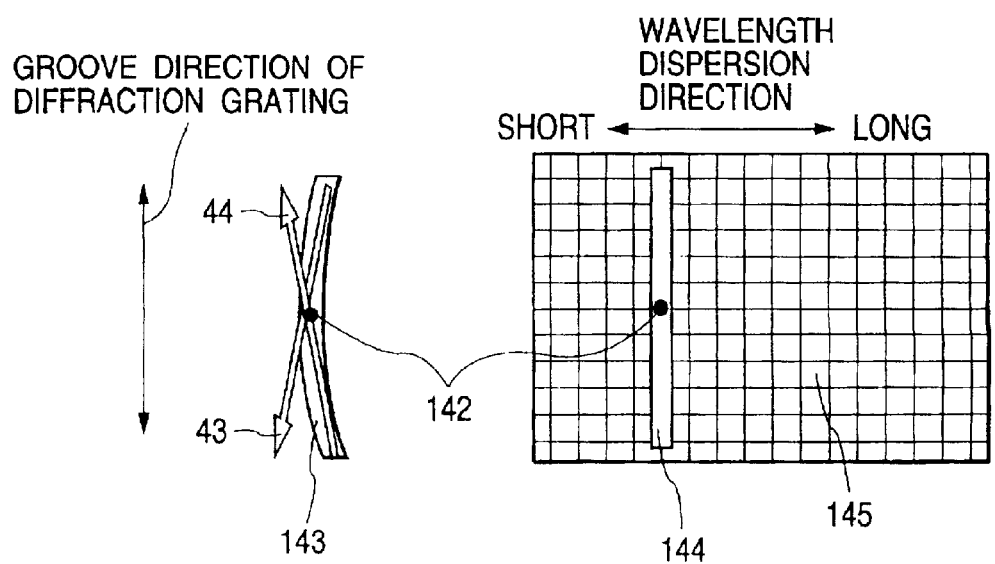

Further, in the present embodiment, since the offset angle of the two laser beams is not zero, the following effect can be observed. Due to the inherent characteristic of a granting a formed image 141 on the CCD of a monochromatic emission light source 140 which is in parallel with the grooves in the grating distorts toward long wavelength as positions move away from the center 142 of the image (which corresponds to the center axis of the fluorescent condenser lens 54 in the embodiment 2) as illustrated in FIG. 12A. FIG. 12B is a skeleton diagram of the intensity distribution 143 of the incident laser beam onto the capillary array according to the present embodiment. The grating and the CCD are arranged in such a manner that the grooves of the grating and grids 145 of pixels in the CCD are parallel with the laser optical axis as in embodiment 2.

In other words, the above will be explained as follows, when injecting urea aqueous solution of density 8M and refractive index of 1.41 into all of the capillaries and noting a certain specific Raman band effected by the incident laser beam 43 as the excitation light source, the position of formed image of the Raman band from the first capillary in the image spectrumed by the grating moves toward a short wavelength in comparison with the position of formed image of the Raman band from the $16^{th}$ capillary, further, when noting a certain specific Raman band effected by the incident laser beam 44 as the excitation light source, the position of formed image of the Raman band from the $16^{th}$ capillary in the image spectrumed by the grating moves toward a short wavelength in comparison with the position of formed image of the Raman band from the first capillary.

This is because that the offset angle of the two laser beams is not zero and the intensities of the respective laser beams attenuate as they propagate through the 16 pieces of capillaries. FIG. 12B shows an image 144 on the CCD from such light emission source in which the inherent distortion by the grating is canceled out (however, it should be noted that the image is inverted). Therefore, through the elimination of the image distortion an advantage is obtained that the data analysis taken out from the CCD is facilitated.

Embodiment 5

FIGS. 13A through 13D show a skeleton diagram of the embodiment 5 according to the present invention, in which only the vicinity of the detection portion of the capillary array and the laser beam introduction route thereof are illustrated and the illustration of the elements such as a shutter and a filter used for the laser beam is omitted. The present embodiment is a combination of the embodiments 2 and 4. Like the embodiment 4, the two laser beams 43 and 44 are on the array face 22, and these two laser beams are not in coaxial but offset by 0.86°. However, unlike the embodiment 4, the standard optical axis 28 does not correspond to the bisector of the two laser beams and the rotation angles of the grating and the CCD in the fluorescent detection system are the same as in the embodiment 2. All of the center axes of transmitted light 124 after the incident laser beam 43 transmits through the capillaries, transmitted light 122 after the laser beam 44 transmits through the capillaries, reflection light 125 of the laser beam 43 by the capillaries and reflection light 126 of the laser beam 44 by the capillaries are designed so as not to be in coaxial with the incident laser beams 43 and 44. These incident laser beams, the transmitted lights and reflection lights run substantially in parallel at the outer sides of the condenser lenses with respect to the capillary array. Further, the structure of the capillary array in the present embodiment is identical as that in the embodiments 1 through 4. Still further, the name of parts and the definition of terms in the present embodiment are the same as those in the embodiments 1 through 4 if not otherwise defined.

Figure 14A:
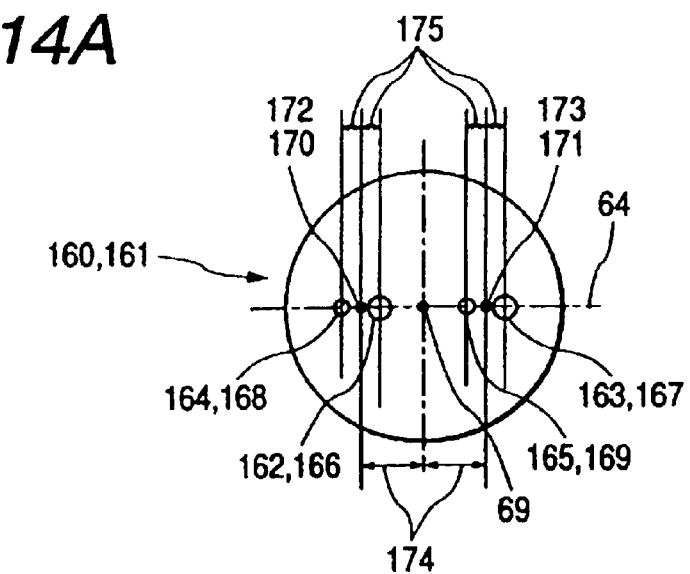
FIGS. 14A and 14B are diagrams showing plane structures of pin hole plates according to another embodiment of the present invention.

In order to realize such optical axis layout an optical axis adjustment is performed as follows by making use of pin hole plates as illustrated in FIG. 14A. At first, the two condenser lenses 45 and 46 are removed from the electrophoresis apparatus and pin hole plates 160 and 161 in which pin holes are formed as illustrated in FIG. 14A are disposed at positions where the laser beam condenser lenses 45 and 46 were respectively disposed.

The position of the pin holes in the pin hole plates is determined as follows depending on an incident angle of the laser beam to the capillaries to be set. There are provided four pin holes for each pin hole plate, in that pin holes 162, 163, 164 and 165 for the pin hole plate 160 and pin holes 166, 167, 168 and 169 for the pin hole plate 161 and two marks for each pin hole plate, in that marks 170 and 171 for the pin hole plate 160 and marks 172 and 173 for the pin hole plate 161. All of these four pin holes and two marks are on the array reference line 64. The distance 174 from the pin hole reference point to the respective marks is determined as X so that the midpoint of the two marks comes to the pin hole reference point 69.

The mark 170 is determined to come to the midpoint of the pin holes 162 and 164 and the mark 171 is determined to come to the midpoint of the pin holes 163 and 165 and distances 175 between the pin holes 162 and 164 and the mark 170 and between the pin holes 163 and 165 and the mark 175 are assumed as dX. Each diameter of the pin holes 162, 166, 163 and 167 is 0.5 mm and each diameter of the pin holes 164, 168, 165 and 169 is 0.2 mm. When assumed that an angle 176 defined by the laser beam 43 and the standard optical axis 28 is (T1−dT1) and an angle 177 defined by the laser beam 44 and the standard optical axis 28 is (T1+dT1) the offset angle of the two laser beams is given as 2dT1. Further, when assuming that (distance between the condenser lens 45 and the first capillary 65)+(the width of the capillary array)/2 is L1, an adjustment is performed so that the following equations stand;

$$X = L1 \times \tan(T1)$$

$$dX = L1 \times \tan(dT1)$$

Namely, in the present embodiment, when selecting as L1=52.9 mm (the distance between the condenser lens 45 and the first capillary 65 is 50 mm and the width of the capillary array is 5.8 mm), T1=2.1° and dT1=0.43°, X is determined as 1.9 mm and dX is determined as 0.4 mm. In the same way the position of the pin holes 166, 167, 168 and 169 on the pin hole plate 161 is determined.

After removing the capillary array from a capillary array attachment position 75, the laser beam optical axis is adjusted in such a manner that the laser beam 43 passes through the pin holes 162 and 166 respectively in the pin hole plates disposed at two positions, the laser beam 44 passes through the pin holes 163 and 167 and the two laser beams run substantially in parallel as illustrated in FIG. 13A. After removing the pin hole plate 161, the condenser lens 46 is set. In this instance, the position of the condenser lens 46 is determined as follows. X, Y and Z axes are assumed as illustrated in FIGS. 13A through 13D. With regard to Y and Z axes, like optimization as in the embodiment 2 is performed.

Figure 14B:
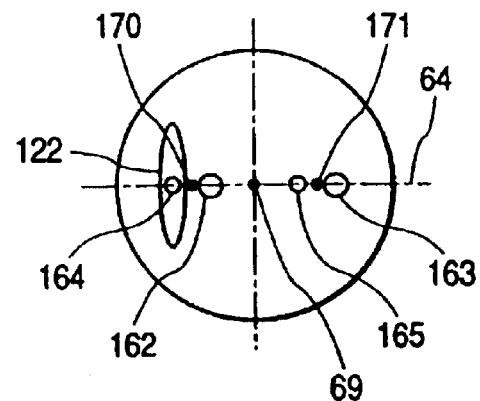

With regard to X axis direction, an adjustment is performed so that the center of transmission light 122 when the laser beam 44 transmits through the capillary array comes to the center of the pin hole 164 in the pin hole plate 160 as illustrated in FIG. 14B. Then, after removing the pin hole plate 160 the condenser lens 45 is set. With regard to X, Y and Z axes, the optimization of the lens position is performed in the like manner as in the embodiment 3. With the above sequence and by making use of the pin hole plates in which X and dX are properly set, the incident angle of the laser beam to the capillaries can be set as desired.

Figure 14C:
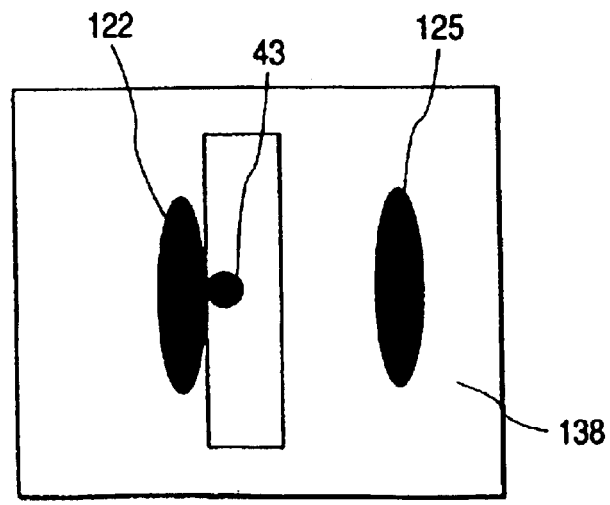

Further, like the embodiment 4, the slits 138 and 139 are attached. On the slit 138 spots of the transmitted light 122 and the reflection light 125 are observed as illustrated in FIG. 14C. The slit 138 is disposed so as to transmits the incident laser beam 43 but to interrupt the transmitted light 122 and the reflection light 125. The slit 139 is likely disposed so as to transmit the incident laser beam 44 but to interrupt the transmitted light 124 and the reflection light 126. Thus, the intensity of returning light is reduced and thereby instability of the laser oscillation is prevented.

Further, as a modification of the present embodiment 5 a combination of the embodiments 3 and 4 can be provided.

Embodiment 6

FIGS. 15A through 15D show an embodiment 6 according to the present embodiment which is a combination of the embodiments 2, 3 and 4 above. All of the center axes of transmitted light 124 after the incident laser beam 43 transmits through the capillaries, transmitted light 122 after the laser beam 44 transmits through the capillaries, reflection light 125 of the laser beam 43 by the capillaries and reflection light 126 of the laser beam 44 by the capillaries are designed so as not to be in coaxial with the incident laser beams 43 and 44. Further, the structure of the capillary array in the present invention is identical as that in the embodiment 2. Still further, the name of parts and the definition of terms in the present embodiment are the same as those in the embodiments 1 through 5 if not otherwise defined.

Figure 16A:
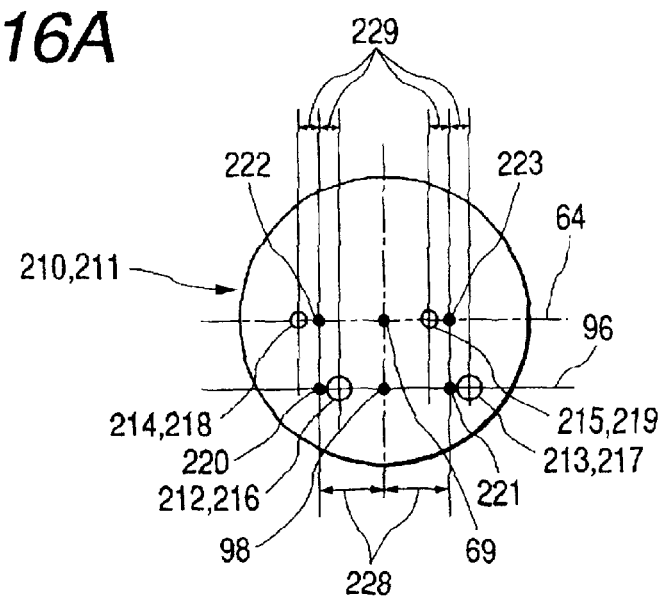
FIGS. 16A and 16B are diagrams showing plane structures of pin hole plates according to still another embodiment of the present invention and FIG. 16C shows a light intensity distribution on the plane of the pin hole plate.

In order to realize such optical axis layout an optical axis adjustment is performed as follows by making use of pin hole plates as illustrated in FIG. 16A. At first, the two condenser lenses 45 and 46 are removed from the electrophoresis apparatus and pin hole plates 210 and 211 in which pin holes are formed as illustrated in FIG. 16A are disposed at positions where the laser beam condenser lenses 45 and 46 were respectively disposed. The position of the pin holes in the pin hole plates is determined as follows depending on an incident angle of the laser beam to the capillaries to be set. There are four pin holes for each pin hole plate, in that pin holes 212, 213, 214 and 215 for the pin hole plate 210 and pin holes 216, 217, 218 and 219 for the pin hole plate 211, and four marks for each pin hole plate, in that marks 220, 221, 222 and 223 for the pin hole plate 210 and marks 224, 225, 226 and 227 for the pin hole plate 211. The centers of the pin holes 212 and 213 and of the marks 220 and 221 are on the elevation angle line 96 which is away from the array reference line 64 by a distance Y. The centers of the pin holes 214 and 215 and of the marks 222 and 223 are on the array reference line 64. The midpoint of the marks 220 and 221 is designed to come to the elevation angle line reference point 98 and the midpoint of the marks 222 and 223 is designed to come to the pin hole reference point 69. The distances 228 from the elevation angle line reference point 98 to the marks 220 and 221 and from the pin hole reference point 69 to the marks 222 and 223 are determined equal and designated as X. The distances 229 between the pin hole 212 and the mark 220, the pin hole 213 and the mark 221, the pin hole 214 and the mark 222, and the pin hole 215 and the mark 223 are all equal and designated as dX. When assuming that angles defined by orthogonal projections of the incident laser beams on the array face 22 and the standard optical axis 28 are (T1−dT1) for the laser beam 43 and (T1+dT1) for the laser beam 44, an angle 230 defined by a plane formed by the elevation angle reference point and the center axis of the first capillary and the array face as T2, (distance between the condenser lens 45 and the first capillary 65)+(width of the capillary array)/2 as L1 and the distance between the condenser lens 45 and the first capillary as L2, an adjustment is performed so that the following equations stand;

$X = L1 \times \tan(T1)$ $dX = L1 \times \tan(dT1)$ $Y = L2 \times \tan(T2)$

Namely, in the present embodiment, when selecting as L1=52.9 mm, T1=2.1°, T2=2.2°, dT1=0.43°, X is determined as 1.9 mm, dX is determined as 0.4 mm and Y is determined as 1.9 mm. Further, each diameter of the pin holes 212 and 213 is determined as 0.5 mm and each diameter of the pin holes 214 and 215 is determined as 0.2 mm. Still further, the pin holes 216, 217, 218 and 219 on the pin hole plate 211 are set in the same manner as above.

Figure 16B:
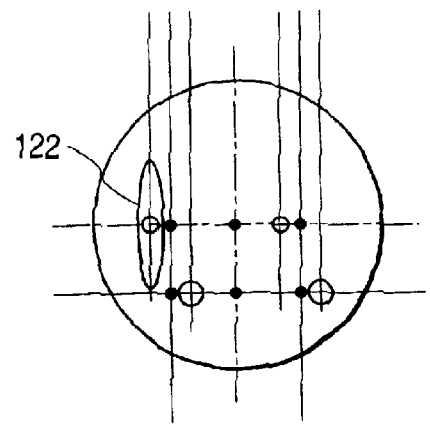

The laser beam optical axis is adjusted in such a manner that the laser beam 43 passes through the pin holes 212 and 216 respectively in the pin hole plates disposed at two positions, the laser beam 44 passes through the pin holes 213 and 217 and the two laser beams run substantially in parallel as illustrated in FIG. 15A. After removing the pin hole plate 211, the condenser lens 46 is set. In this instance, the position of the condenser lens 46 is determined as follows. X, Y and Z axes are assumed as illustrated in FIGS. 15A through 15D. With regard to Y and Z axes, like optimization as in the embodiment 5 is performed. With regard to X axis direction, an adjustment is performed so that the center of transmission light 122 when the laser beam 44 transmits through the capillary array comes to the center of the pin hole 214 in the pin hole plate 210 as illustrated in FIG. 16B.

Then, after removing the pin hole plate 210 the condenser lens 45 is set. With regard to X, Y and Z axes, the optimization of the lens position is performed in the like manner as in the embodiment 5. With the above sequence and by making use of the pin hole plates in which X, dX and Y are properly set, the incident angle of the laser beam to the capillaries can be set as desired.

Figure 16C:
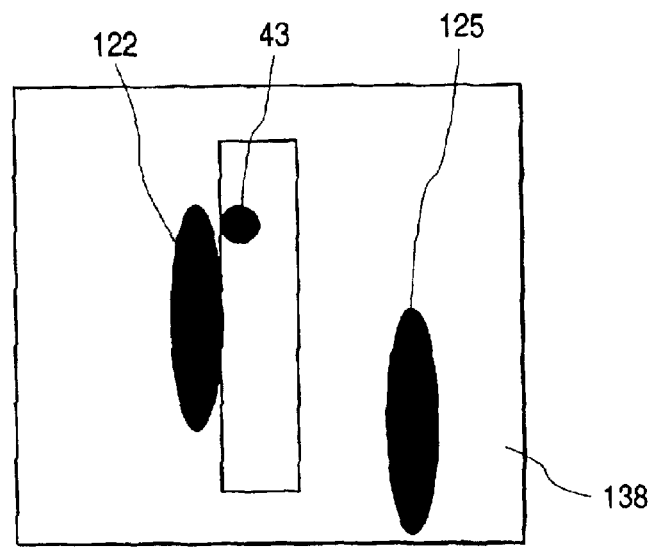

Further, like the embodiment 5, the slits 138 and 139 are attached. On the slit 138 spots of the transmitted light 122 and the reflection light 125 are observed as illustrated in FIG. 16C. The slit 138 is disposed so as to transmits the incident laser beam 43 but to interrupt the transmitted light 122 and the reflection light 125. The slit 139 is likely disposed so as to transmit the incident laser beam 44 but to interrupt the transmitted light 124 and the reflection light 126. Thus, the intensity of returning light is reduced and thereby instability of the laser oscillation is prevented.

According to the present invention, instability of laser oscillation due to reflection and/or returning light when laser beam is irradiated onto the multi capillary array can be prevented.

What is claimed is:

1. A capillary array electrophoresis apparatus comprising:
    a capillary array constituted by a plurality of capillaries for containing electrophoresis medium for separating specimen, said capillary array including a detection portion formed by at least parts of the plurality of capillaries, said parts being aligned substantially parallel;
    a power source adapted to apply a voltage between respective ends of the capillaries; and
    an irradiation and detection system including a laser oscillator which irradiates no less than one laser beam across the detection portion and detects light emitted from the specimen,
    wherein the laser beam is incident on an outermost end capillary in the detection portion in an inclined manner so that an optical path of the incident laser beam into the end capillary differs from an optical path of a laser beam reflected from the detection portion, and the laser beam propagates successively to adjacent capillaries.

2. A capillary array electrophoresis apparatus according to claim 1, wherein the capillary is a glass tube covered with a coating and at least the coating on the capillary in the detection portion is removed.

3. A capillary array electrophoresis apparatus according to claim 1, wherein an optical axis of the laser beam incident on the end capillary is inclined with respect to a line that is perpendicular to a center axis of the end capillary on a plane formed by center axes of the capillaries in the detection portion.

4. A capillary array electrophoresis apparatus according to claim 3, wherein an optical axis of the laser beam incident on the end capillary is inclined by about 2° with respect to a line that is perpendicular to a center axis of the end capillary on a plane formed by center axes of the capillaries in the detection portion.

5. A capillary array electrophoresis apparatus according to claim 1, wherein the irradiation and detection system includes a laser beam preventing member having a hole for passing a laser beam irradiated into the detection portion and for interrupting a laser beam reflected from the detection portion.

6. A capillary array electrophoresis apparatus according to claim 1, wherein the irradiation and detection system includes a lens which converges a laser beam parallel with a line that is perpendicular to a center axis of the end capillary on a plane formed by center axes of the capillaries in the detection portion, and upon displacement, said lens is capable of inclining the laser beam with respect to the perpendicular line.

7. A capillary array electrophoresis apparatus according to claim 1, wherein the irradiation and detection system includes a wavelength dispersion mechanism which disperses a wavelength of light radiated from the detection portion in a direction that is substantially perpendicular to an optical axis of the laser beam crossing the detection portion.

8. A capillary array electrophoresis apparatus according to claim 1, wherein the wavelength dispersion mechanism includes at least a grating or a prism.

9. A capillary array electrophoresis apparatus according to claim 1, wherein the irradiation and detection system includes a two dimensional CCD for detecting a light radiated from the detection portion and having a grid of pixels configured substantially parallel with an optical axis of the laser beam crossing the detection portion.

10. A capillary array electrophoresis apparatus comprising:
  a capillary array constituted by a plurality of capillaries for containing electrophoresis medium for separating specimen, said capillary array including a detection portion formed by at least parts of the capillaries, said parts being aligned substantially parallel;
  a power source adapted to apply a voltage between respective ends of the capillaries; and
  an irradiation and detection system including a laser oscillator which irradiates no less than one laser beam across the detection portion and detects light emitted from the specimen,
  wherein an optical axis of the laser beam incident on an outermost end capillary is inclined with respect to a line that is perpendicular to a center axis of the end capillary on a plane formed by center axes of the capillaries in the detection portion, and the laser beam propagates successively to adjacent capillaries.

11. A capillary array electrophoresis apparatus according to claim 10, wherein each capillary is a glass tube covered with a coating and at least the coating on the capillary in the detection portion is removed.

12. A capillary array electrophoresis apparatus according to claim 10, wherein an optical axis of the laser beam incident on the end capillary is inclined by about 2° with respect to a line that is perpendicular to a center axis of the end capillary on a plane formed by center axes of the capillaries in the detection portion.

13. A capillary array electrophoresis apparatus according to claim 10, wherein the irradiation and detection system includes a laser beam preventing member having a hole for passing a laser beam irradiated into the detection portion and for interrupting a laser beam reflected from the detection portion.

14. A capillary array electrophoresis apparatus according to claim 10, wherein the irradiation and detection system includes a lens which converges a laser beam parallel with a line that is perpendicular to a center axis of the end capillary on a plane formed by center axes of the capillaries in the detection portion, and upon displacement, said lens is capable of inclining the laser beam with respect to the perpendicular line.

15. A capillary array electrophoresis apparatus according to claim 10, wherein the irradiation and detection system includes a wavelength dispersion mechanism for dispersing a wavelength of light generated from the specimen in a direction that is substantially perpendicular to an optical axis of the laser beam crossing the detection portion.

16. A capillary array electrophoresis apparatus according to claim 15, wherein the wavelength dispersion mechanism includes at least a grating or a prism.

17. A capillary array electrophoresis apparatus according to claim 10, wherein the irradiation and detection system includes a two dimensional CCD for detecting a light radiated from the detection portion and having a grid of pixels that are almost parallel with an optical axis of the laser beam crossing the detection portion.

18. A capillary array electrophoresis apparatus comprising:
  a capillary array constituted by a plurality of capillaries for containing electrophoresis medium for separating specimen, said capillary array including a detection portion formed by at least parts of the capillaries, said parts being aligned substantially parallel;
  a power source adapted to apply a voltage between respective ends of the capillaries; and
  an irradiation and detection system including a laser oscillator for irradiating laser beams across the detection portion respectively from both sides of the detection portion and for detecting light emitted from the specimen,
  wherein the laser beams are incident on outermost end capillaries at both sides in the detection portion in an inclined manner so that an optical path of the incident laser beam into each end capillary differs from an optical path of a laser beam reflected from the detection portion, and the laser beams propagate successively to adjacent capillaries.

19. A capillary array electrophoresis apparatus according to claim 18, wherein each capillary is a glass rube covered with a coating and at least the coating on the capillary in the detection portion is removed.

20. A capillary array electrophoresis apparatus according to claim 18, wherein an optical axis of the laser beam incident on the end capillary is inclined with respect to a line that is perpendicular to a center axis of the end capillary on a plane formed by center axes of the capillaries in the detection portion.

21. A capillary array electrophoresis apparatus according to claim 18, wherein the irradiation and detection system includes a laser beam preventing member having a hole, said preventing member for passing a laser beam irradiated into the detection portion and for interrupting at least one of a laser beam reflected from the detection portion and a laser beam having crossed the detection portion.

22. A capillary array electrophoresis apparatus according to claim 18, wherein the irradiation and detection system includes a lens for converging a laser beam parallel with a line that is perpendicular to a center axis of the end capillary on a plane formed by center axes of the capillaries in the detection portion, and upon displacement, said lens is capable of inclining the laser beam with respect to the perpendicular line.

23. A capillary array electrophoresis apparatus according to claim 18, wherein the irradiation and detection system includes a wavelength dispersion mechanism for eliminating an image distortion at a light generation point in the detection portion.

24. A capillary array electrophoresis apparatus according to claim 23, wherein the wavelength dispersion mechanism includes at least a grating or a prism.

25. A capillary array electrophoresis apparatus according to claim 18, wherein the irradiation and detection system includes a two dimensional CCD for detecting a light radiated from the detection portion and having a grid of pixels, said grid being almost parallel to an optical axis of the laser beam crossing the detection portion.

26. A capillary array electrophoresis apparatus according to claim 18, wherein optical axes of the laser beams incident on the detection portion are inclined with respect to a plane formed by center axes of the capillaries in the detection portion.

27. A capillary array electrophoresis apparatus according to claim 18, wherein optical axes of the laser beams incident on the detection portion are inclined by about 2° with respect to a plane formed by center axes of the capillaries in the detection portion.

28. A capillary array electrophoresis apparatus according to claim 18, wherein the laser beams crossing the detection portion are not in parallel so that the laser beams having crossed the detection portion are prevented from reaching the laser oscillator.

29. A capillary array electrophoresis apparatus according to claim 18, wherein respective inclinations, of optical axes of the laser beams incident on the detection portion, with respect to a line that is perpendicular to a center axis of the end capillary on a plane formed by center axes of the capillaries in the detection portion, differ so that the laser beams having crossed the detection portion are prevented from reaching the laser oscillator.

30. A capillary array electrophoresis apparatus according to claim 18, wherein laser beams crossing the detection portion intersect near a center of the detection portion.

31. A capillary array electrophoresis apparatus according to claim 18, wherein the irradiation and detection system includes a grating for optically separating light radiated from the detection portion.

32. A capillary array electrophoresis apparatus comprising:
a capillary array constituted by a plurality of capillaries for containing electrophoresis medium for separating specimen, said capillary array including a detection portion formed by at least parts of the capillaries, said parts being aligned substantially parallel;
a power source adapted to apply a voltage between respective ends of the capillaries; and
an irradiation and detection system including a laser oscillator which irradiates laser beams across the detection portion respectively from both sides of the detection portion and detects light emitted from the specimen,
wherein optical axes of the laser beams incident on outermost end capillaries are inclined with respect to a line that is perpendicular to a center axis of the end capillaries on a plane formed by center axes of the capillaries in the detection portion, and the laser beams propagate successively to adjacent capillaries.

33. A capillary array electrophoresis apparatus according to claim 32, wherein each capillary is a glass tube covered with a coating and at least the coating on the capillary in the detection portion is removed.

34. A capillary array electrophoresis apparatus according to claim 32, wherein the irradiation and detection system includes a laser beam preventing member having a hole, said preventing member for passing a laser beam irradiated into the detection portion and for interrupting at least one of a laser beam reflected from the detection portion and a laser beam having crossed the detection portion.

35. A capillary array electrophoresis apparatus according to claim 32, wherein the irradiation and detection system includes a lens for converging a laser beam parallel with a line that is perpendicular to a center axis of the end capillary on a plane formed by center axes of the capillaries in the detection portion, and upon displacement, said lens is capable of inclining the laser beam with respect to the perpendicular line.

36. A capillary array electrophoresis apparatus according to claim 32, wherein the irradiation and detection system includes a wavelength dispersion mechanism for eliminating an image distortion at a light generation point in the detection portion.

37. A capillary array electrophoresis apparatus according to claim 36, wherein the wavelength dispersion mechanism includes at least a grating or a prism.

38. A capillary array electrophoresis apparatus according to claim 32, wherein the irradiation and detection system includes a two dimensional CCD for detecting a light generated from a specimen containing fluorescent pigment, said CCD having a grid of pixels being almost parallel with an optical axis of the laser beam crossing the detection portion.

39. A capillary array electrophoresis apparatus according to claim 32, wherein optical axes of the laser beams incident on the end capillaries are inclined with respect to a plane formed by center axes of the capillaries in the detection portion.

40. A capillary array electrophoresis apparatus according to claim 32, wherein optical axes of the laser beams incident on the end capillaries are inclined by about 2° with respect to a plane formed by center axes of the capillaries in the detection portion.

41. A capillary array electrophoresis apparatus according to claim 32, wherein the laser beams crossing the detection portion are not in parallel so that the laser beams having crossed the detection portion are prevented from reaching the laser oscillator.

42. A capillary array electrophoresis apparatus according to claim 32, wherein respective inclinations, of optical axes of the laser beams incident on the detection portion, with respect to a line that is perpendicular to a center axis of the end capillary on a plane formed by center axes of the capillaries in the detection portion, differ so that the laser beams having crossed the detection portion are prevented from reaching the laser oscillator.

43. A capillary array electrophoresis apparatus according to claim 32, wherein laser beams crossing the detection portion intersect near a center of the detection potion.

44. A capillary array electrophoresis apparatus according to claim 32, wherein the irradiation and detection system includes a grating for optically separating light radiated from the detection portion.

* * * * *